(12) United States Patent
Trayanova et al.

(10) Patent No.: US 10,363,100 B2
(45) Date of Patent: Jul. 30, 2019

(54) SYSTEMS AND METHODS FOR PATIENT-SPECIFIC MODELING OF THE HEART FOR PREDICTION OF TARGETS FOR CATHETER ABLATION OF VENTRICULAR TACHYCARDIA IN PATIENTS WITH IMPLANTABLE CARDIOVERTER DEFIBRILLATORS

(71) Applicant: The Johns Hopkins University, Baltimore, MD (US)

(72) Inventors: Natalia A. Trayanova, Baltimore, MD (US); Adityo Prakosa, Baltimore, MD (US); Sohail Zahid, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/563,354

(22) PCT Filed: May 12, 2016

(86) PCT No.: PCT/US2016/032187
§ 371 (c)(1),
(2) Date: Sep. 29, 2017

(87) PCT Pub. No.: WO2016/183365
PCT Pub. Date: Nov. 17, 2016

(65) Prior Publication Data
US 2018/0078312 A1  Mar. 22, 2018

Related U.S. Application Data

(60) Provisional application No. 62/160,536, filed on May 12, 2015.

(51) Int. Cl.
*A61B 34/10* (2016.01)
*G06T 11/00* (2006.01)
(Continued)

(52) U.S. Cl.
CPC .............. *A61B 34/10* (2016.02); *G06F 19/00* (2013.01); *G06T 7/0012* (2013.01); *G06T 7/11* (2017.01);
(Continued)

(58) Field of Classification Search
CPC combination set(s) only.
See application file for complete search history.

(56) References Cited

U.S. PATENT DOCUMENTS

| | | | |
|---|---|---|---|
| 8,538,550 B2 * | 9/2013 | Stubbs | A61N 1/37 607/31 |
| 9,717,415 B2 * | 8/2017 | Cohen | A61B 5/0044 |

(Continued)

FOREIGN PATENT DOCUMENTS

WO    WO-2014-071249 A1    5/2014

OTHER PUBLICATIONS

International Search Report in International Application No. PCT/US2016/032187, dated Aug. 8, 2016.

(Continued)

*Primary Examiner* — Anand P Bhatnagar
(74) *Attorney, Agent, or Firm* — Venable LLP; Henry J. Daley

(57) ABSTRACT

A system, computer-readable medium and method can include receiving three-dimensional imaging data of a subject's heart, the subject having an ICD, wherein the ICD causes an imaging artifact in the three-dimensional imaging data that includes regions that are free of the artifact and regions that are affected by the artifact; segmenting the regions that are free of the artifact into a plurality of normal tissue regions and remodeled tissue regions for the subject; extrapolating from the regions that are free of the artifact to provide extrapolated three-dimensional imaging data corresponding to the regions that are affected by the artifact; and (Continued)

simulating at least one of electrophysiological or electromechanical activity of the subject's heart using the segmented and extrapolated three-dimensional imaging data, the simulating including providing a preselected alteration of electrophysiological or electromechanical behavior of the subject's heart for a target of said subject-specific cardiac ablation procedure.

24 Claims, 15 Drawing Sheets

(51) Int. Cl.
    *G06T 19/00*     (2011.01)
    *G16H 50/50*     (2018.01)
    *G06T 7/11*     (2017.01)
    *G16H 30/20*     (2018.01)
    *G06T 7/00*     (2017.01)
    *G06T 17/00*     (2006.01)
    *G06F 19/00*     (2018.01)
    *A61B 90/00*     (2016.01)

(52) U.S. Cl.
    CPC .............. *G06T 11/00* (2013.01); *G06T 17/00* (2013.01); *G06T 19/00* (2013.01); *G16H 30/20* (2018.01); *G16H 50/50* (2018.01); *A61B 2034/105* (2016.02); *A61B 2090/374* (2016.02); *A61B 2090/378* (2016.02); *A61B 2090/3762* (2016.02); *G06T 2207/10028* (2013.01); *G06T 2207/30048* (2013.01); *G06T 2210/41* (2013.01)

(56) References Cited

U.S. PATENT DOCUMENTS

| | | | |
|---|---|---|---|
| 9,855,384 B2 * | 1/2018 | Cohen ................... | A61B 90/37 |
| 10,052,495 B2 * | 8/2018 | Ben-Haim ............ | G06T 7/0012 |
| 2011/0224962 A1 * | 9/2011 | Goldberger ........... | G06T 7/0012 |
| | | | 703/11 |
| 2013/0069945 A1 * | 3/2013 | Ledesma Carbayo ...................... | |
| | | | G06T 15/08 |
| | | | 345/420 |
| 2014/0023256 A1 * | 1/2014 | Nazarian ............... | A61B 5/7203 |
| | | | 382/131 |
| 2014/0088943 A1 * | 3/2014 | Trayanova .......... | A61B 5/04021 |
| | | | 703/11 |
| 2014/0122048 A1 * | 5/2014 | Vadakkumpadan ........................ | |
| | | | A61B 5/7275 |
| | | | 703/11 |
| 2016/0022375 A1 * | 1/2016 | Blake ................... | A61B 5/7455 |
| | | | 600/424 |
| 2017/0217102 A1 * | 8/2017 | Mansi ................. | B29C 67/0088 |

OTHER PUBLICATIONS

Adelstein et al., "Scar Burden by Myocardial Perfusion Imaging Predicts Echocardiographic Response to Cardiac Resynchronization Therapy in Ischemic Cardiomyopathy," *Am Heart J* 153m 195-12 (2007).
Akar et al., "Dynamic Changes in Conduction Velocity and Gap Junction Properties During Development of Pacing-Induced Heart Failure," Am J Physiol Heart Circ Physiol 293, H1223-30 (2007).
Akar et al., "Mechanisms Underlying Conduction Slowing and Arrhythmogenesis in Nonischemic Dilated Cardiomyopathy," *Circ Res* 95, 717-25 (2004).
Aliot et al., "EHRA/HRS Expert Consensus on Catheter Ablation of Ventricular Arrhythmias: Developed in a partnership with the European Heart Rhythm Association (EHRA), a Registered Branch of the European Society of Cardiology (ESC), and the Heart Rhythm Society (HRS); in collaboration with the American College of Cardiology (ACC) and the American Heart Association (AHA)," Europace. 11, 771 <last_page> 817 (2009; 2009).
Ansalone et al., "Doppler myocardial imaging to evaluate the effectiveness of pacing sites in patients receiving biventricular pacing," *J Am Coll Cardiol* 39, 489-99 (2002).
Arevalo et al., "Tachycardia in post-infarction hearts: insights from 3d image-based ventricular models," PLoS One, 8, p. e68872 (2013).
Arheden et al., "Reperfused rat myocardium subjected to various durations of ischemia: estimation of the distribution volume of contrast material with echo-planar MR imaging Radiology," 215, 520-528 (2000).
Ashikaga et al., "Magnetic resonance-based anatomical analysis of scar-related ventricular tachycardia: implications for catheter ablation," Circ. Res. 101, 939-947 (2007).
Ashikaga et al., "Electromechanical analysis of infarct border zone in chronic myocardial infarction," *Am J Physiol Heart Circ Physiol* 289, H1099-105 (2005).
Ashikaga et al., "Feasibility of image-based simulation to estimate ablation target in human ventricular arrhythmia," Heart Rhythm, 10, pp. 1109-1116 (2013).
Auricchio et al., "Clinical Efficacy of Cardiac Resynchronization Therapy Using Left Ventricular Pacing in Heart Failure Patients Stratified by Severity of Ventricular Conduction Delay," *J Am Coll Cardiol* 42, 2109-16 (2003).
Auricchio et al., "Effect of Pacing Chamber and Atrioventricular Delay on Acute Systolic Function of Paced Patients with Congestive Heart Failure. The Pacing Therapies for Congestive Heart Failure Study Group. The Guidant Congestive Heart Failure Research Group," Circulation 99, 2993-3001 (1999).
Bax et al., "Left Ventricular Dyssynchrony Predicts Response and Prognosis after Cardiac Resynchronization Therapy," J Am Coll Cardiol 44, 1834-40 (2004).
Bayer et al., "Novel rule based algorithm for assigning myocardial fiber orientation to computation heart models," Ann Biomed Eng. , (in submission) (2012).
Becker et al., "Ventricular excitation in experimental left bundle branch block," *Am Heart J* 55, 54756 (1958).
Beg et al., "Computational cardiac anatomy using MRI Magn," Reson. Med. 52, 1167-1174 (2004).
Beshai et al., "Cardiac-resynchronization therapy in heart failure with narrow QRS complexes," *N Eng J Med* 357, 2461-2471 (2007).
Bleeker et al., "Effect of Posterolateral Scar Tissue on Clinical and Echocardiographic Improvement after Cardiac Resynchronization Therapy," *Circulation* 113, 969-76 (2006b).
Bleeker et al., "Left Ventricular Dyssynchrony in Patients with Heart Failure: Pathophysiology, Diagnosis and Treatment," *Nat Clin Pract Cardiovasc Med* 3, 213-9 (2006a).
Brugada et al., "Nonsurgical transthoracic epicardial radiofrequency ablation: an alternative in incessant ventricular tachycardia," J. Am. Coll. Cardiol. 41, 2036-2043 (2003).
Butter et al., "Effect of Resynchronization Therapy Stimulation Site on the Systolic Function of Heart Failure Patients," Circulation 104, 3026-9 (2001).
Butter et al., "Should Stimulation Site Be Tailored in the Individual Heart Failure Patient?" Am J Cardiol 86, 144K-151K (2000).
Callans et al., "Efficacy of radiofrequency catheter ablation for ventricular tachycardia in healed myocardial infarction," Am. J. Cardiol. 82, 429-432 (1998).
Cheng et al., "Heterogeneity of left ventricular wall thickening mechanisms," Circulation 118, 713-721 (2008).
Choi et al., "Transmural Extent of Acute Myocardial Infarction Predicts Long-Term Improvement in Contractile Function," *Circulation* 104, 1101-7 (2001).
Chung et al., "Results of the Predictors of Response to CRT (PROSPECT) trial," *Circulation* 117, 2608-2616 (2008).
Cleland et al., "The Effect of Cardiac Resynchronization on Morbidity and Mortality in Heart Failure," *N. Engl J Med* 352, 1539-49 (2005).

(56) References Cited

OTHER PUBLICATIONS

Clerc, "Directional differences of impulse spread in trabecular muscle from mammalian heart. J. Physiol," (Lond.). 255, 335-346 (1976).
Constantino et al., "Optimal cardiac resynchronization therapy is achieved by pacing from the LV region with the longest electromechanical delay," *Heart Rhythm* 7, S164-165.
Cordeiro et al., "Transmural heterogeneity of calcium activity and mechanical function in the canine left ventricle," Am J Physiol Heart Circ Physiol 286, H1471-9 (2004).
de Bakker et al., "Reentry as a cause of ventricular tachycardia in patients with chronic ischemic heart disease: electrophysiologic and anatomic correlation," Circulation. 77, 589-606 (1988).
Delacretaz et al., "Catheter Ablation of Ventricular Tachycardia in Patients with Coronary Heart Disease", Journal of Pacing and Clinical Electrophysiology, vol. 24, No. 8, 1261-1277 (Aug. 2001).
De Maria et al., "Long-Term Outcomes After Cryoablation for Ventricular Tachycardia During Surgical Treatment of Anterior Ventricular Aneurysms Pacing and Clinical Electrophysiology," 28, S168-171 (2005).
Derval et al., "Optimizing hemodynamics in heart failure patients by systematic screening of left ventricular pacing sites: the lateral left ventricular wall and the coronary sinus are rarely the best sites," J Am Coll Cardiol 55, 566-75 (2010).
Dong et al., "Impact of heart rhythm status on registration accuracy of the left atrium for catheter ablation of atrial fibrillation," J. Cardiovasc. Electrophysiol. 18, 1269-1276 (2007).
Dun et al., "Dynamic remodeling of K+ and Ca2+ currents in cells that survived in the epicardial border zone of canine healed infarcted heart," Am. J. Physiol. Heart Circ. Physiol. 287, H1046-54 (2004).
Estner, et al., "The Critical Isthmus Sites of Ischemic Ventricular Tachycardia are in Zones of Tissue Heterogeneity," Visualized by Magnetic Resonance Imaging Heart Rhythm. (2011).
Fauchier et al., "Interventricular and Intraventricular Dyssynchrony in Idiopathic Dilated Cardiomyopathy: A Prognostic Study with Fourier Phase Analysis of Radionuclide Angioscintigraphy," J Am Coll Cardiol 40, 2022-30 (2002).
Fauchier et al., "Reliability of QRS Duration and Morphology on Surface Electrocardiogram to Identify Ventricular Dyssynchrony in Patients with Idiopathic Dilated Cardiomyopathy," Am J Cardiol 92, 341-4 (2003).
Fish et al., "Potential Proarrhythmic Effects of Biventricular Pacing," J Am Coll Cardiol 46, 2340-7 (2005).
Frapier et al., "Large encircling cryoablation without mapping for ventricular tachycardia after anterior myocardial infarction: Long-term outcome," J. Thorac. Cardiovasc. Surg. 116, 578 <last_page> 583 (1998).
Fung et al., "Effect of left ventricular lead concordance to the delayed contraction segment on echocardiographic and clinical outcomes after cardiac resynchronization therapy," J Cardiovasc Electrophysiol 20, 530-5 (2009).
Gima et al., "Ionic Current Basis of Electrocardiographic Waveforms: A Model Study," Circ Res. 90, 889-896 (2002).
Gurev et al., "Models of cardiac electromechanics based on individual hearts imaging data: image-based electromechanical models of the heart," Biomech. Model. Mechanobiol. 10, 295-306 (2011).
Gurev et al., "Distribution of electromechanical delay in the heart: insights from a three-dimensional electromechanical model," Biophys J 99, 745-54 (2010).
Helm et al., "Evidence of Structural Remodeling in the Dys-synchronous Failing Heart," *Circ Res* 98, 125-32 (2006).
Helm et al., "Three-Dimensional Mapping of Optimal Left Ventricular Pacing Site for Cardiac Resynchronization," *Circulation* 115, 953-61 (2007).
Hooks et al., "Laminar Arrangement of Ventricular Myocytes Influences Electrical Behavior of the Heart," *Circ Res* 101, e103-12 (2007).
Howard et al., "Improvement in pump function with endocardial biventricular pacing increases with activation time at the left ventricular pacing site in failing canine hearts," *Am J Physiol Heart Circ Physiol* 301, H1447-55 (2011).
Jiang et al., "Delayed rectifier K currents have reduced amplitudes and altered kinetics in myocytes from infarcted canine ventricle," Cardiovasc. Res. 48, 34-43 (2000).
Kaab et al., "Ionic Mechanism of Action Potential Prolongation in Ventricular Myocytes from Dogs with Pacing-Induced Heart Failure," Circ Res 78, 262-73 (1996).
Kass, "Cardiac Resynchronization Therapy," J Cardiovasc Electrophysiol 16 Suppl 1, S35-41 (2005).
Khan et al., "Effect of radiofrequency catheter ablation of ventricular tachycardia on left ventricular function in patients with prior myocardial infarction," J. Interv. Card. Electrophysiol. 7, 243-247 (2002).
Lardo et al., "Visualization and temporal/spatial characterization of cardiac radiofrequency ablation lesions using magnetic resonance imaging," Circulation. 102, 698-705 (2000).
Larson et al., "Analysis of electrically-induced reentrant circuits in a sheet of myocardium," Ann Biomed Eng. 31, 768-80 (2003).
Leclercq et al., "Left Ventricular Lead Insertion Using a Modified Transseptal Catheterization Technique: A Totally Endocardial Approach for Permanent Biventricular Pacing in End-Stage Heart Failure," *Pacing Clin Electrophysiol* 22, 1570-5 (1999).
Leclercq et al., "Systolic improvement and mechanical resynchronization does not require electrical synchrony in the dilated failing heart with left bundle-branch block," *Circulation* 106, 1760-3 (2002).
LeGrice et al., "Transverse Shear Along Myocardial Cleavage Planes Provides a Mechanism for Normal Systolic Wall Thickening," *Circ Res* 77, 182-93 (1995).
Lindner et al., "Cardiac efficiency and oxygen consumption measured with 11 C-acetate PET after long-term cardiac resynchronization therapy," *J Nucl Med* 47, 378-83 (2006).
Lindner et al., "Effect of cardiac resynchronization therapy on global and regional oxygen consumption and myocardial blood flow in patients with non-ischaemic and ischaemic cardiomyopathy," *Eur Heart J* 26, 70-6 (2005).
Lloyd-Jones, D. et al., "Heart Disease and Stroke Statistics-2009 Update: A Report from the American Heart Association Statistics Committee and Stroke Statistics Subcommittee," Circulation 119, 480-6 (2009).
Luo et al., "A dynamic model of the cardiac ventricular action potential. II. Afterdepolarizations, triggered activity, and potentiation," Circ Res. 74, 1097-1113 (1994).
Marijianowski et al., "Dilated Cardiomyopathy Is Associated with an Increase in the Type I/Type III Collagen Ratio: A Quantitative Assessment," J Am Coll Cardiol 25, 1263-72 (1995).
McDowell et al., "Susceptibility to arrhythmia in the infarcted heart depends on myofibroblast density," Biophys. J. 101, 1307-1315 (2011).
Mesubi et al., "Impact of ICD Artifact Burden on Late Gadolinium Enhancement Cardiac MR Imaging in Patients Undergoing Ventricular Tachycardia Ablation. Pacing and Clinical Electrophysiology," 37, pp. 1274-1283 (2014).
Miyazaki et al., "Dyssynchrony indices to predict response to cardiac resynchronization therapy: a comprehensive prospective single-center study," Circ Heart Fail 3, 565-73 (2010).
Moreno et al., "A computational model to predict the effects of class I anti-arrhythmic drugs on ventricular rhythms," Sci. Transl. Med. 3, 98ra83 (2011).
Nazarian, "CMR for Mapping the Missing Dimension in Ventricular Tachycardia Ablation," JACC: Cardiovascular Imaging 3 (3), pp. 286-288 (2010).
Nelson et al., "Left Ventricular or Biventricular Pacing Improves Cardiac Function at Diminished Energy Cost in Patients with Dilated Cardiomyopathy and Left Bundle-Branch Block," Circulation 102, 3053-9 (2000).
O'Rourke et al., "Mechanisms of Altered Excitation-Contraction Coupling in. Canine Tachycardia-Induced Heart Failure, I: Experimental Studies," Circ Res 84, 562-70. (1999).
Peters et al., "Myocardial architecture and ventricular arrhythmogenesis," Circulation. 97, 1746-1754 (1998).

(56) References Cited

OTHER PUBLICATIONS

Pitzalis et al., "Cardiac Resynchronization Therapy Tailored by Echocardiographic Evaluation of Ventricular Asynchrony," *J Am Coll Cardiol* 40, 1615-22 (2002).
Pu et al., "Alterations of Na$A-F$ currents in myocytes from epicardial border zone of the infarcted heart. A possible ionic mechanism for reduced excitability and postrepolarization refractoriness," Circ. Res. 81, 110-119 (1997).
Reddy et al., "Prophylactic Catheter Ablation for the Prevention of Defibrillator Therapy," N Engl J Med, 357, pp. 2657-2665 (2007).
Rice et al., "Approximate model of cooperative activation and crossbridge cycling in cardiac muscle using ordinary differential equations," *Biophys J* 95, 2368-90 (2008).
Roes et al., "Infarct tissue heterogeneity assessed with contrast-enhanced MRi predicts spontaneous ventricular arrhythmia in patients with ischemic cardiomyopathy and implantable cardioverter-defibrillator," Circ. Cardiovasc. Imaging. 2, 183-190 (2009).
Russell et al., "Mechanism of prolonged electromechanical delay in late activated myocardium during left bundle branch block," *Am J Physiol Heart Circ Physiol* 301, H2334-43 (2011).
Sasaki et al., "Quantitative Assessment of Artifacts on Cardiac Magnetic Resonance Imaging of Patients With Pacemakers and Implantable Cardioverter-Defibrillators, Circulation: Cardiovascular Imaging," 4, pp. 662-670 (2011).
Sasano et al., "Molecular ablation of ventricular tachycardia after myocardial infarction," 12, 1256-1258 (2006).
Schmidt et al., "Infarct tissue heterogeneity by magnetic resonance imaging identifies enhanced cardiac arrhythmia susceptibility in patients with left ventricular dysfunction," Circulation. 115, 2006-2014 (2007).
Schuleri et al., "Characterization of Peri-Infarct Zone Heterogeneity by Contrast-Enhanced Multidetector Computed Tomography," J. Am. Coll. Cardiol. 53, 1699 <last_page> 1707 (2009).
Soejima et al., "Catheter ablation in patients with multiple and unstable ventricular tachycardias after myocardial infarction: short ablation lines guided by reentry circuit isthmuses and sinus rhythm mapping," Circulation. 104, 664-669 (2001).
Sosa et al., "Nonsurgical transthoracic epicardial catheter ablation to treat recurrent ventricular tachycardia occurring late after myocardial infarction," J. Am. Coll. Cardiol. 35, 1442-1449 (2000).
Spragg et al., "Optimal left ventricular endocardial pacing sites for cardiac resynchronization therapy in patients with ischemic cardiomyopathy," *J Am Coll Cardiol* 56, 774-81 (2010).
Sutton et al., "Effect of Cardiac Resynchronization Therapy on Left Ventricular Size and Function in Chronic Heart Failure," *Circulation* 107, 1985-90 (2003).
Suffoletto et al., "Novel speckle-tracking radial strain from routine black-and-white echocardiographic images to quantify dyssynchrony and predict response to cardiac resynchronization therapy," *Circulation* 113, 960-8 (2006).

Suga, "Ventricular energetics," *Physiol Rev* 70, 247-77 (1990).
Sutton et al., "Sustained Reverse Left Ventricular Structural Remodeling with Cardiac Resynchronization at One Year Is a Function of Etiology: Quantitative Doppler Echocardiographic Evidence from the Multicenter Insync Randomized Clinical Evaluation (MIRACLE)," *Circulation* 113, 266-72 (2006).
Tusscher et al., AJP-HeartCirc.Phys., 286:1673-1698 (2004).
Tyberg et al., "Effects of hypoxia on mechanics of cardiac contraction," Am J Physiol 218, 1780-8 (1970).
Ukkonen et al., "Effect of cardiac resynchronization on myocardial efficiency and regional oxidative metabolism," Circulation 107, 28-31 (2003).
Ursell et al., "Structural and electrophysiological changes in the epicardial border zone of myocardial infarcts during infarct healing," Circ. Res. 56, 436-452 (1985).
Usyk et al., "Relationship between Regional Shortening and Asynchronous Electrical Activation in a Three-Dimensional Model of Ventricular Electromechanics," J Cardiovasc Electrophysiol 14, S196-202 (2003).
Vadakkumpadan et al., "Image-based models of cardiac structure in health and disease Wiley Interdisciplinary Reviews: Systems Biology and Medicine," 2, 489-506 (2010).
van Deursen et al., "Left ventricular endocardial pacing improves resynchronization therapy in canine left bundle-branch hearts," Circ Arrhythm Electrophysiol 2, 580-7 (2009).
Vigmond et al., "Computational tools for modeling electrical activity in cardiac tissue," J. Electrocardiol. 36, 69-74 (2003).
Walker et al., "MRI-based finite-element analysis of left ventricular aneurysm," Am J Physiol Heart Circ Physiol 289, H692-700 (2005).
Wellens, "Catheter ablation of cardiac arrhythmias: usually cure, but complications may occur. Circulation," 99, pp. 195-197 (1999).
White et al., "Delayed Enhancement Magnetic Resonance Imaging Predicts Response to Cardiac Resynchronization Therapy in Patients with Intraventricular Dyssynchrony," *J Am Coll Cardiol* 48, 1953-60 (2006).
Wu et al., "Changes in Titin Isoform Expression in Pacing-Induced Cardiac Failure Give Rise to Increased Passive Muscle Stiffness," Circulation 106, 1384-9 (2002).
Yan et al., "Characterization of the peri-infarct zone by contrast-enhanced cardiac magnetic resonance imaging is a powerful predictor of post-myocardial infarction mortality," Circulation. 114, 32-39 (2006).
Yao et al., "Remodeling of gap junctional channel function in epicardial border zone of healing canine infarcts," Circ. Res. 92, 437-443 (2003).
Yu et al., "Tissue Doppler Echocardiographic Evidence of Reverse Remodeling and Improved Synchronicity by Simultaneously Delaying Regional Contraction after Biventricular Pacing Therapy in Heart Failure," Circulation 105, 438-45 (2002).
Zhong et al., "On the accuracy of CartoMerge for guiding posterior left atrial ablation in man Heart Rhythm," 4, 595-602 (2007).

\* cited by examiner

SYSTEMS AND METHODS FOR PATIENT-SPECIFIC MODELING OF THE HEART FOR PREDICTION OF TARGETS FOR CATHETER ABLATION OF VENTRICULAR TACHYCARDIA IN PATIENTS WITH IMPLANTABLE CARDIOVERTER DEFIBRILLATORS

CROSS REFERENCE TO RELATED APPLICATIONS

This application is a U.S. National Stage Application under 35 U.S.C. § 371 of PCT/US2016/032187, filed on May 12, 2016, the entire content of which is hereby incorporated by reference and this application claims the benefit of U.S. Provisional Patent Application No. 62/160,536, filed May 12, 2015, the entire content of which is hereby incorporated by reference.

FEDERAL FUNDING

This invention was made with government support under 1DP1HL123271-01 awarded by the National Institutes of Health. The government has certain rights in the invention.

TECHNICAL FIELD

The present invention relates to systems and methods for subject-specific modeling and simulations of functioning of the subject's heart.

BACKGROUND

Ventricular tachyarrhythmia (VT) frequently occurs in the setting of myocardial infarction (MI). Catheter-based ablation is a promising procedure which has become first-line therapy for many types of cardiac arrhythmias (E. Delacretaz, W. G. Stevenson, Catheter ablation of ventricular tachycardia in patients with coronary heart disease: part I: Mapping. *Pacing Clin. Electrophysiol.* 24, 1261-1277 (2001); K. Soejima, M. Suzuki, W. H. Maisel, C. B. Brunckhorst, E. Delacretaz, L. Blier, S. Tung, H. Khan, W. G. Stevenson, Catheter ablation in patients with multiple and unstable ventricular tachycardias after myocardial infarction: short ablation lines guided by reentry circuit isthmuses and sinus rhythm mapping. *Circulation.* 104, 664-669 (2001)). However, catheter ablation has achieved low levels of success in eliminating MI-related VT; only 58% initial success rate and 71% eventual success rate following repeated procedures, with complications rate as high as 8% of the treated population (D. J. Callans, E. Zado, B. H. Sarter, D. Schwartzman, C. D. Gottlieb, F. E. Marchlinski, Efficacy of radiofrequency catheter ablation for ventricular tachycardia in healed myocardial infarction. *Am. J. Cardiol.* 82, 429-432 (1998)).

The low efficacy of catheter ablation for infarct-related VT stems from the fact that current voltage and pace mapping techniques to identify the targets of ablation are associated with numerous limitations, including ambiguities in correlating maps with anatomy (J. Dong, D. Dalal, D. Scherr, A. Cheema, S. Nazarian, K. Bilchick, I. Almasry, A. Cheng, C. A. Henrikson, D. Spragg, J. E. Marine, R. D. Berger, H. Calkins, Impact of heart rhythm status on registration accuracy of the left atrium for catheter ablation of atrial fibrillation. *J. Cardiovasc. Electrophysiol.* 18, 1269-1276 (2007)), and insufficient resolution in identifying ablation targets, resulting from the point-by-point sampling nature of current mapping techniques (J. Brugada, A. Berruezo, A. Cuesta, J. Osca, E. Chueca, X. Fosch, L. Wayar, L. Mont, Nonsurgical transthoracic epicardial radiofrequency ablation: an alternative in incessant ventricular tachycardia. *J. Am. Coll. Cardiol.* 41, 2036-2043 (2003); E. Sosa, M. Scanavacca, A. d'Avila, F. Oliveira, J. A. Ramires, Nonsurgical transthoracic epicardial catheter ablation to treat recurrent ventricular tachycardia occurring late after myocardial infarction. *J. Am. Coll. Cardiol.* 35, 1442-1449 (2000); H. Zhong, J. M. Lacomis, D. Schwartzman, On the accuracy of CartoMerge for guiding posterior left atrial ablation in man *Heart Rhythm.* 4, 595-602 (2007)). Furthermore, the complex 3D pathways along which the cardiac impulse propagates around/through the zone of infarct during VT, are difficult to reconstruct on the basis of electrical interrogation of ventricular surfaces only (J. M. de Bakker, F. J. van Capelle, M. J. Janse, A. A. Wilde, R. Coronel, A. E. Becker, K. P. Dingemans, N. M. van Hemel, R. N. Hauer, Reentry as a cause of ventricular tachycardia in patients with chronic ischemic heart disease: electrophysiologic and anatomic correlation. *Circulation.* 77, 589-606 (1988); N. Peters, A. Wit, Myocardial architecture and ventricular arrhythmogenesis. *Circulation.* 97, 1746-1754 (1998)). These limitations prolong procedure duration, greatly increasing the risk of chamber perforation, thromboemboli, and radiation overexposure, and limit the success of the therapy.

New approaches that deliver swift and accurate identification of optimal infarct-related VT ablation targets will dramatically improve the efficacy of the therapy and increase its tolerance while reducing post-procedure complications. This will result in a dramatic medical and economic impact on both the lives of patients and the society at large.

In the current state-of-the art, the targets for catheter ablation of VT in patients with myocardial infarction or fibrosis are determined following extensive catheter-based voltage and pace mapping procedures in a clinical electrophysiology (EP) laboratory. This procedure, however, has a very low efficacy. The latter stems from difficulties in correlating electrical maps with anatomy, and from overlooking critical sites needing ablation due to the point-by-point sampling nature of current mapping techniques. These limitations prolong the duration of the procedure, which can last four to twelve hours. Extensive VT ablation often results in excessive and unnecessary tissue damage, and greatly increases the risk associated with the procedure. Our previous invention (U.S. Patent Application Publication No. 2014/0088943, the entire contents of which are incorporated herein by reference) provides a non-invasive method to identify the optimal ablation sites for infarct-related VT by using 3D electrophysiological heart simulation with a model reconstructed from the patient's late gadolinium-enhanced (LGE) MRI image. However, that approach has problems when applied to patients with Implantable Cardioverter Defibrillators (ICDs). Even though the safety and clinical utility of MR imaging at 1.5T in patients with ICD has been demonstrated, the ICD creates an artifact in the LGE-MRI image, hindering the construction of the patient-specific heart model.

Therefore, there remains a need for improved systems and methods for planning patient-specific cardiac procedures for patients with ICDs.

SUMMARY

A computer implemented method of non-invasively simulating a subject-specific cardiac procedure can include: receiving three-dimensional imaging data of a subject's heart, the subject having an ICD, wherein the ICD causes an imaging artifact in the three-dimensional imaging data of said subject's heart, the three-dimensional imaging data including regions that are free of the artifact and regions that are affected by the artifact; segmenting the regions of the three-dimensional imaging data that are free of the artifact into a plurality of normal tissue regions and remodeled tissue regions for the subject; extrapolating from the regions of the three-dimensional imaging data that are free of the artifact to provide extrapolated three-dimensional imaging data corresponding to the regions that are affected by the artifact; and simulating at least one of electrophysiological or electromechanical activity of at least a portion of the subject's heart using the segmented and extrapolated three-dimensional imaging data, the simulating including providing a preselected alteration of at least one of electrophysiological or electromechanical behavior of the subject's heart for a target of the subject-specific cardiac ablation procedure.

A non-transient computer-readable medium can comprise computer-executable code that, when executed by a computer, causes the computer to perform: receiving three-dimensional imaging data of a subject's heart, the subject having an ICD, wherein the ICD causes an imaging artifact in the three-dimensional imaging data of the subject's heart, the three-dimensional imaging data including regions that are free of the artifact and regions that are affected by the artifact; segmenting the regions of the three-dimensional imaging data that are free of the artifact into a plurality of normal tissue regions and remodeled tissue regions for the subject; extrapolating from the regions of the three-dimensional imaging data that are free of the artifact to provide extrapolated three-dimensional imaging data corresponding to the regions that are affected by the artifact; and non-invasively simulating at least one of electrophysiological or electromechanical activity of at least a portion of the subject's heart using the segmented and extrapolated three-dimensional imaging data, the simulating including providing a preselected alteration of at least one of electrophysiological or electromechanical behavior of the subject's heart for a target of the subject-specific cardiac ablation procedure.

A system comprising a computer, said computer comprising a non-transient computer-readable medium can comprise computer-executable code that, when executed by the computer, causes the computer to perform: receiving three-dimensional imaging data of a subject's heart, the subject having an ICD, wherein the ICD causes an imaging artifact in the three-dimensional imaging data of the subject's heart, the three-dimensional imaging data including regions that are free of the artifact and regions that are affected by the artifact; segmenting the regions of the three-dimensional imaging data that are free of said artifact into a plurality of normal tissue regions and remodeled tissue regions for the subject; extrapolating from the regions of the three-dimensional imaging data that are free of the artifact to provide extrapolated three-dimensional imaging data corresponding to the regions that are affected by the artifact; and non-invasively simulating at least one of electrophysiological or electromechanical activity of at least a portion of the subject's heart using the segmented and extrapolated three-dimensional imaging data, the simulating including providing a preselected alteration of at least one of electrophysiological or electromechanical behavior of the subject's heart for a target of the subject-specific cardiac ablation procedure.

Additional features, advantages, and embodiments of the invention are set forth or apparent from consideration of the following detailed description, drawings and claims. Moreover, it is to be understood that both the foregoing summary of the invention and the following detailed description are examples and intended to provide further explanation without limiting the scope of the invention as claimed.

BRIEF DESCRIPTION OF THE DRAWINGS

Further objectives and advantages of our previous invention will become apparent from a consideration of the description, drawings—which include color—and examples.

DETAILED DESCRIPTION

Figures 1A, 1B, 1C, 1D, 1E, 1F, 1G:
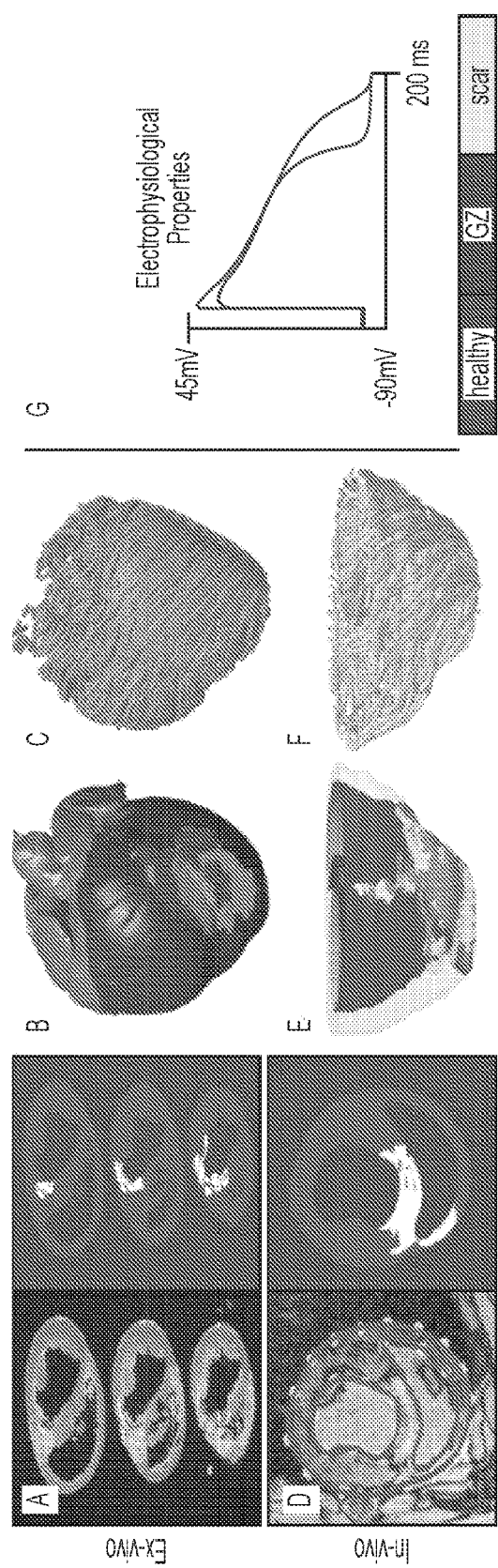
FIGS. 1A-1G show the model creation pipeline according to an embodiment of the current invention. A. Ex-vivo MRIs of an infarcted canine heart with corresponding segmentation. B. 3D model with epicardium rendered semi-transparent. C. Streamline representation of fibers obtained from DTMRI. D. In-vivo MRI of infarcted pig heart with corresponding segmentation. E. Model with epicardium rendered semi-transparent. F. Streamlines of approximated fibers. G. Action potentials of healthy myocytes and GZ cells.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Individualized heart models, reconstructed from LGE MRI scans of patients without ICDs, have shown promise in predicting the targets of infarct related ventricular tachycardia (VT) ablation. (Ashikaga et al. 2013). However, most patients who undergo VT ablation have ICDs which cause image artifacts in the MRI data. (Mesubi et al. 2014). Some embodiments of the current invention overcome this limitation of the previous approach. In addition, some examples demonstrate, retrospectively, that patient specific modeling of VTs in ventricles with ICD artifact can accurately predict optimal ablation sites according to embodiments of the current invention.

Implantable Cardioverter Defibrillators (ICDs) can provide protection from sudden cardiac death due to ventricular tachycardia (VT). To reduce painful and often inappropriate ICD shocks, catheter ablation is frequently a necessary adjunctive therapy for patients with recurrent VT that is resistant to drug therapy. However, despite significant clinical advances in techniques for VT ablation, success rates remain limited. We have previously developed a novel technique to identify non-invasively the optimal ablation targets in VT patients with myocardial infarction. However, that approach has problems when applied to patients with ICDs because of the artifact that the ICD creates in the MRI image. The MRI image is used to construct the patient-specific heart model and predict the optimal targets of ablation, and an image artifact thus constitutes a major limitation. Some embodiments of the current invention overcome this limitation.

In the current state-of-the art, the targets for catheter ablation of VT in patients with myocardial infarction or fibrosis are determined following extensive catheter-based voltage and pace mapping procedures in a clinical electrophysiology (EP) laboratory. This procedure, however, has a very low efficacy. The latter stems from difficulties in correlating electrical maps with anatomy, and from overlooking critical sites needing ablation due to the point-by-point sampling nature of current mapping techniques. These limitations prolong the duration of the procedure, which can last four to twelve hours. Extensive VT ablation often results in excessive and unnecessary tissue damage, and greatly increases the risk associated with the procedure. Previous application U.S. Patent Application Publication No. 2014/0088943 provides a non-invasive method to identify the optimal ablation sites for infarct-related VT by using 3D electrophysiological heart simulation with a model reconstructed from the patient's late gadolinium-enhanced (LGE) MRI image. However, that approach has problems when applied to patients with ICDs. Even though the safety and clinical utility of MR imaging at 1.5T in patients with ICD has been demonstrated, the ICD creates an artifact in the LGE-MRI image, hindering the construction of the patient-specific heart model.

Some embodiments of the current invention can overcome this problem by estimating the image area affected by artifact, and including it in the reconstruction of 3D patient ventricular model. In an embodiment of the current invention, the left ventricular (LV) myocardium area affected by artifact, delineated based on the 3D radial distance from the ICD, is manually reconstructed, and assumed to contain normal tissue. However, the general concepts of the current invention are not limited to only manual reconstruction. The general concepts of the current invention are also not limited to only left ventricle. The right ventricle can also be obstructed in the MRI by the ICD shadow. Outside this area, standard image processing classifies tissue as normal, passive scar, or remodeled border (or gray) zone based on pixel intensity. A model suitable for electrophysiological simulation is then completed by incorporating this information. An embodiment of the current invention also includes a system to compare the predicted ablation sites to the clinical sites when it is used in a retrospective setting. The clinical ablation sites recorded in the CARTO electro anatomical mapping (EAM) system are loaded and projected to the simulation model. Analysis of the proximity between the clinical and the predicted ablation sites is then performed. This can be part of a retrospective analysis to verify results. In other words, in some embodiments, the retrospective analysis is not performed in the clinic since the analysis will be prospective, i.e., ablation will not be performed before we predict the targets.

EXAMPLES

The following describes further concepts of some embodiments of the current invention by way of examples. The general concepts of the current invention are not limited to the particular examples. The references cited in the figures of this section are listed at the end of this section.

Figure 8:
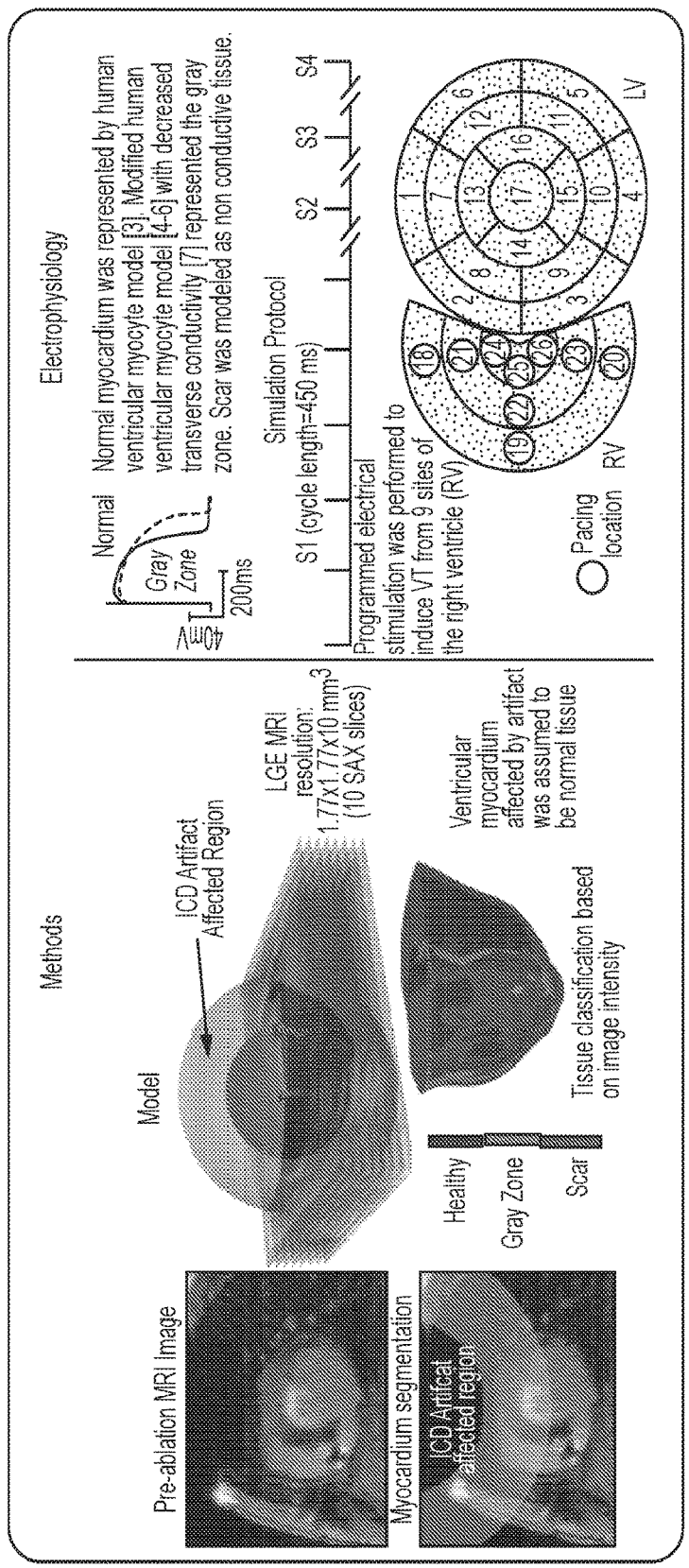
FIG. 8 shows methods of using the simulating a myocardium having an ICD artifact, according to an embodiment of the invention.
Figure 9:
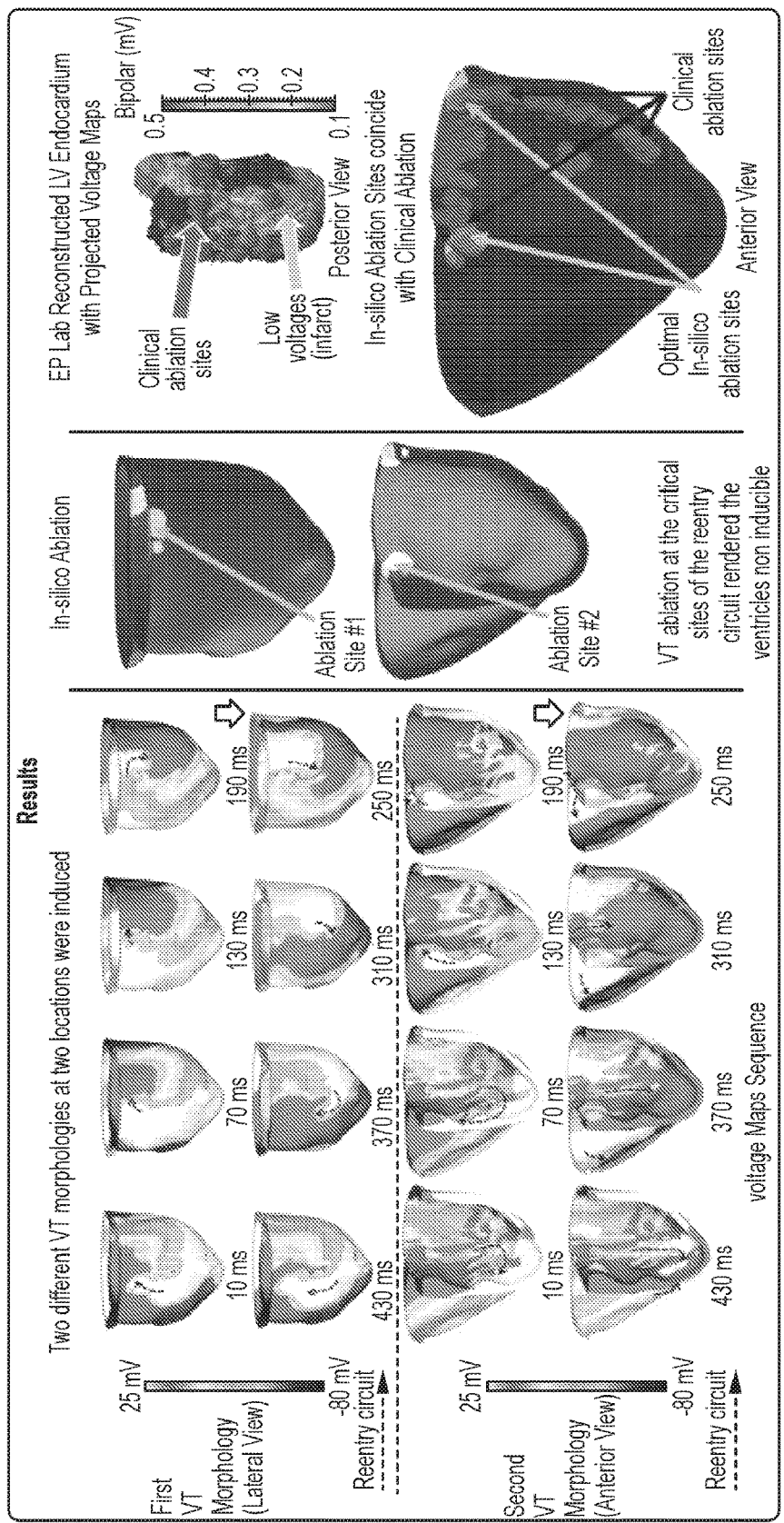
FIG. 9 shows a model reconstruction and VT induction simulation, according to an embodiment of the invention.
Figure 10:
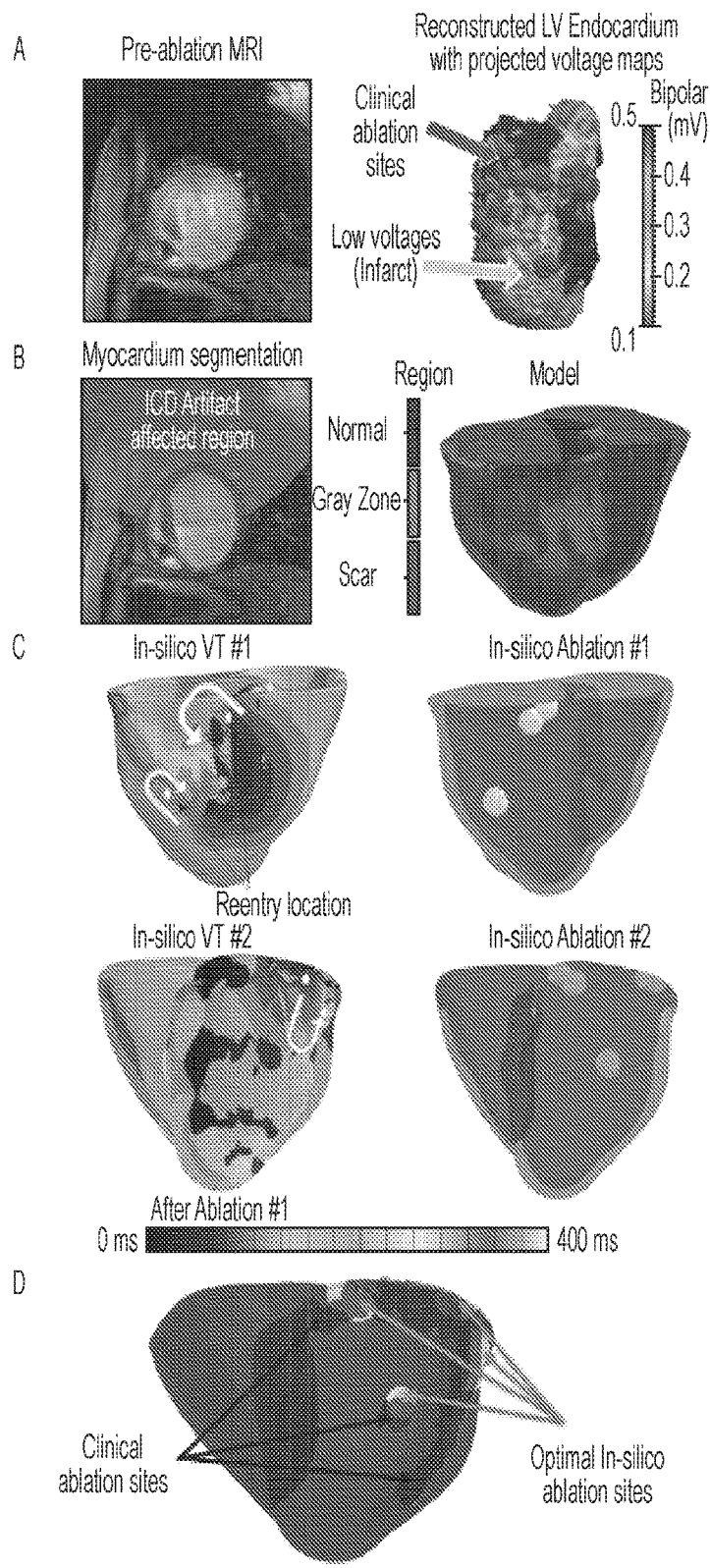
FIGS. 10A-10D shows methods and results of simulating a myocardium having an ICD artifact, according to an embodiment of the invention.
Figure 11:
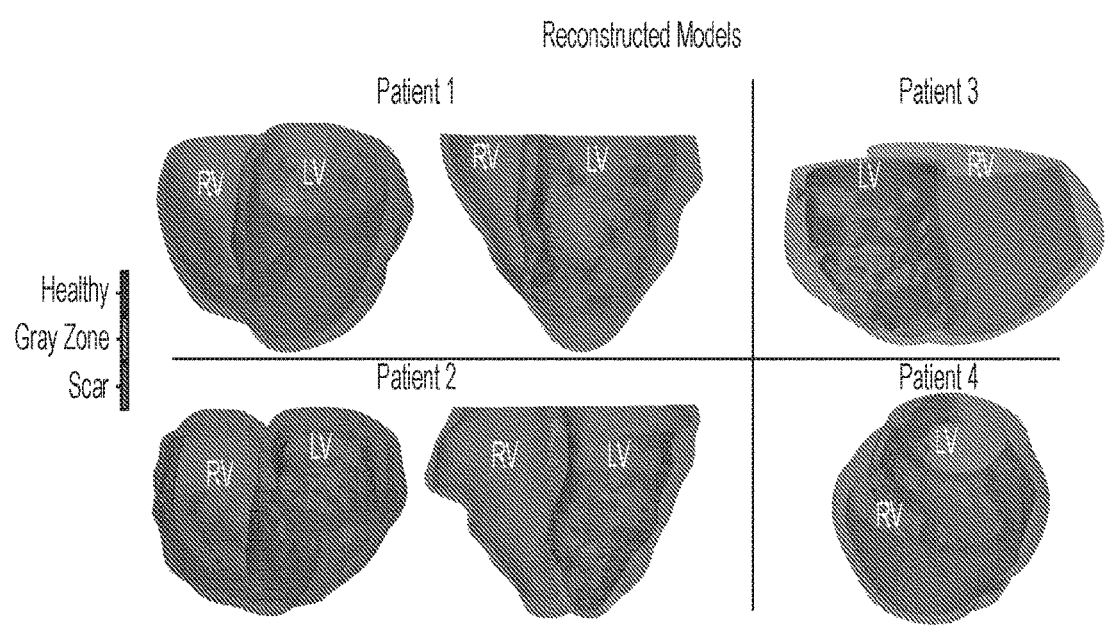
FIG. 11 shows a reconstructed 3D computational model of patient's hearts, according to an embodiment of the invention.
Figure 12:
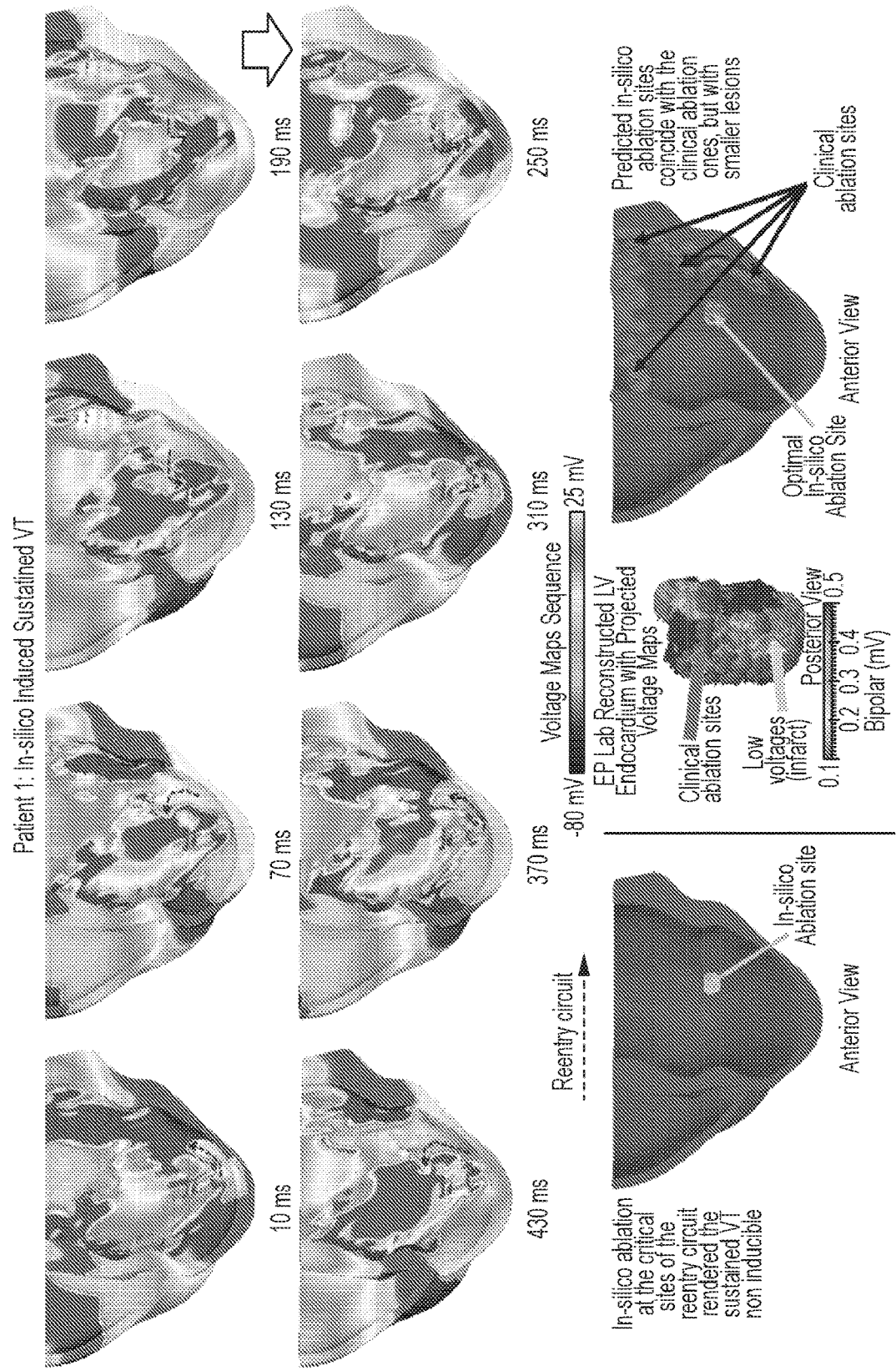
FIG. 12 shows results for a patient, according to an embodiment of the invention.
Figure 13:
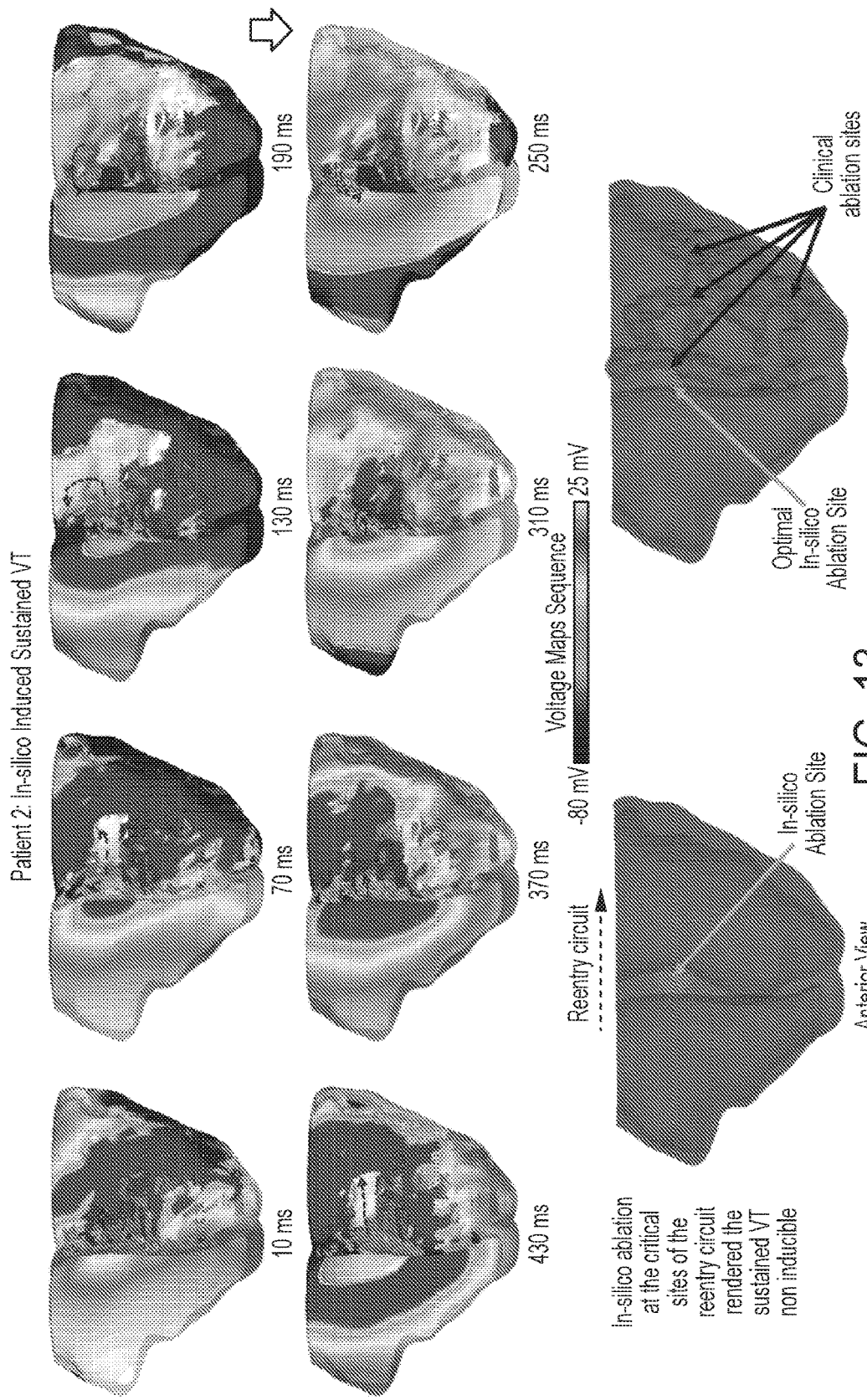
FIG. 13 shows results for a patient, according to an embodiment of the invention.
Figure 14:
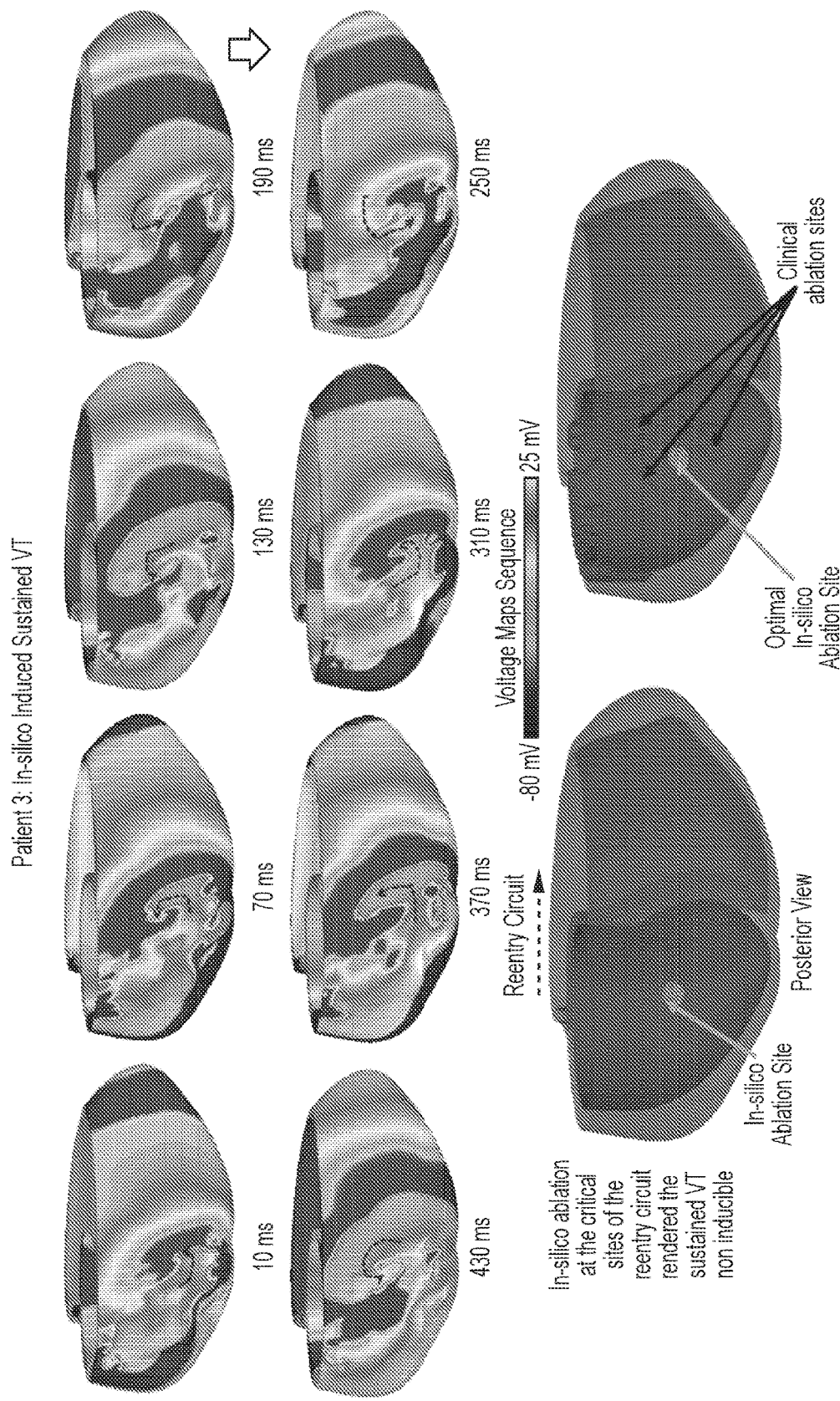
FIG. 14 shows results for a patient, according to an embodiment of the invention.
Figure 15:
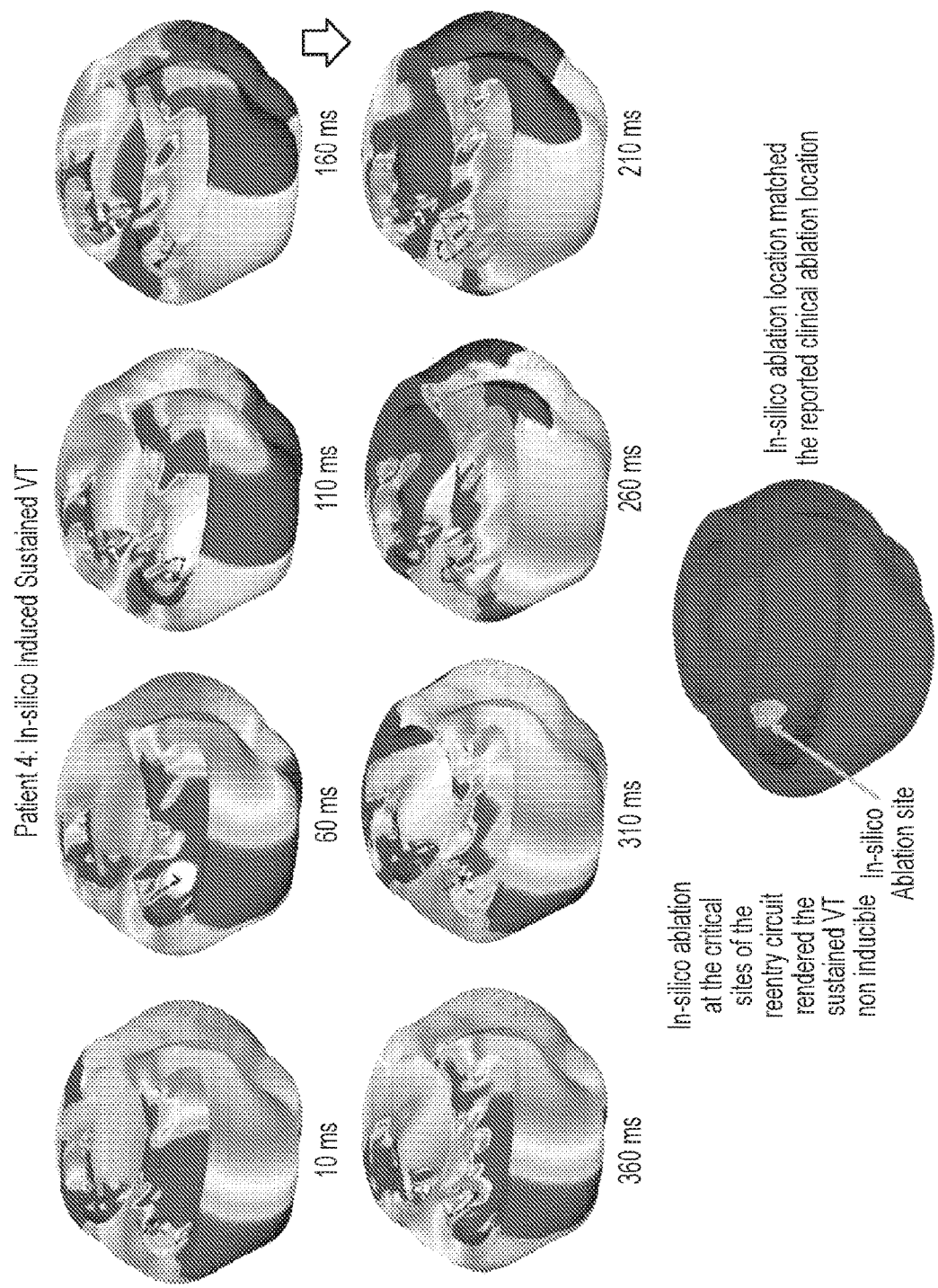
FIG. 15 shows results for a patient, according to an embodiment of the invention.

As shown in FIG. 8, methods of embodiments can include four patients with ICDs and infarct-related ventricular tachycardia (VT) undergoing LGE MRI prior to clinical ablation. 3-D computational models of the patients' hearts were generated from short axis MRI scans (FIGS. 8 and 9). The anterior LV area affected by artifact, delineated based on the radial distance from the ICD, was manually reconstructed, and assumed to contain normal tissue. Outside this area, standard image processing classified tissue as normal, passive scar, or remodeled gray zone based on pixel intensity. Once the model was completed, in-silico programmed electrical stimulation from 9 sites in the right ventricle (RV) was used to induce VTs, and VT circuit analysis identified ablation targets.

As shown in FIG. 9, models can successfully predict VT circuits in regions not affected by artifact (FIGS. 12-15), even when a substantial portion of the heart was affected by artifact, as much as 70% (Table 1).

TABLE 1

Amount of artifact affecting MRI

| Patient | LV Artifact Burden |
|---------|--------------------|
| Patient 1 | 63% |
| Patient 2 | 0% |
| Patient 3 | 70% |
| Patient 4 | 3% |

In silico, programmed electrical stimulation induced sustained VTs for all models; ablation of the VT morphologies at the critical sites of the reentry rendered the ventricles not inducible of sustained VTs; ablation was done by modeling the targets as non-excitable tissue. The optimal simulation-predicted ablation lesions fell within the clinical ones, but were smaller in size.

Conclusions: Results can demonstrate that personalized ventricular models can accurately predict infarct-related VT circuits. In silico analysis of VTs in patients with ICD and posterior infarcts can successfully identify the optimal ablation targets non-invasively. The optimal simulation-predicted ablation lesions fell within the clinical ones, but were smaller in size.

Patient-specific simulation guided ablation could lead to reduction in time, expense and complication rate of clinical VT ablation procedure, and result in increased success rate.

Models successfully predicted VT circuits in regions not affected by artifact, even when most part of the heart was affected by artifact, even when most part of the heart was affected by artifact, as much as 70%. Some embodiments of the current invention can overcome the limitation of the LGE-MRI ICD artifact, which hinders the construction of the patient-specific heart model, by estimating the image area affected by artifact, and including it in the reconstruction of 3D patient ventricular model. The ventricular myocardial wall segmentation relies on the prominent boundaries of the visible myocardial wall and extrapolates this information to the area occluded by the ICD shadow. This was done by using the variational implicit interpolation within CardioViz3D software, which used the user defined control points placed on the visible boundaries of the myocardial wall. Based on the testing on four datasets with ICDs, this approach allowed the reconstruction of the complete ventricular myocardial wall. Since the ICD artifact affects the LGE-MR image beyond the ICD shadow and perturbs the classification of the myocardial tissue (scar, gray zone, and normal), an embodiment of the current invention estimates the affected region based on the 3D radial distance from the ICD. The reconstructed myocardium area within this region can be assumed to contain normal tissue. Outside this area, standard image processing classifies tissue as normal, passive scar, or remodeled gray zone based on pixel intensity. When the shadow is away from the infarct, it can be assumed that the shadow is normal tissue. A model suitable for electrophysiological simulation is then completed by incorporating this information in the reconstructed ventricular myocardium.

Another approach to reconstruct the wall under the ICD shadow, particularly when it covers a bigger part of the myocardium, is to use a reconstruction approach based on a template or atlas where an atlas is fitted to the visible myocardium wall in the image. Anatomical landmarks can be used to globally register the atlas to the patient's myocardium in the image by using an affine transformation. In the image region where the myocardium wall is obscured by the ICD artifact, the atlas can provide the information on the variability of the wall geometry. The information can then be used in the myocardium wall reconstruction. Another option for dealing with the artifact is to use a machine learning approach. A machine learning algorithm can be trained to classify the myocardium wall and artifact within the image, and then the classification can be applied to estimate the myocardium wall in new dataset(s).

Some embodiments of the current invention build on embodiments as described in U.S. Patent Application Publication No. 2014/0088943, the content of which is hereby incorporated herein in its entirety. In that patent application, we introduce a novel multiscale electrophysiological modeling methodology which we term "virtual electrophysiology (EP) lab," and we apply it to the prediction of the optimal targets of catheter ablation of infarct-related monomorphic ventricular tachycardia (VT) in individual hearts. The determination of what constitutes an optimal target of VT ablation is based on a novel mechanistic understanding of the organization of VT in myocardial infarction (MI). Predicting where these optimal ablation targets are located in an individual heart with its specific infarct morphology is based on MRI-based multiscale computational modeling of electrophysiology in that heart according to some embodiments of the current invention.

We can take advantage of advanced image-processing and computational-anatomy tools (H. Ashikaga, T. Sasano, J. Dong, M. M. Zviman, R. Evers, B. Hopenfeld, V. Castro, R. H. Helm, T. Dickfeld, S. Nazarian, J. K. Donahue, R. D. Berger, H. Calkins, M. R. Abraham, E. Marban, A. C. Lardo, E. R. McVeigh, H. R. Halperin, Magnetic resonance-based anatomical analysis of scar-related ventricular tachycardia: implications for catheter ablation Circ. Res. 101, 939-947 (2007); M. F. Beg, P. A. Helm, E. McVeigh, M. I. Miller, R. L. Winslow, Computational cardiac anatomy using MRI Magn. Reson. Med. 52, 1167-1174 (2004)), a high-throughput pipeline for MRI-based individualized heart model generation (F. Vadakkumpadan, H. Arevalo, A. J. Prassl, J. Chen, F. Kickinger, P. Kohl, G. Plank, N. Trayanova, Image-based models of cardiac structure in health and disease Wiley Interdisciplinary Reviews: Systems Biology and Medicine. 2, 489-506 (2010)), and sophisticated numerical simulation and analysis approaches (E. Vigmond, M. Hughes, G. Plank, L. J. Leon, Computational tools for modeling electrical activity in cardiac tissue. J. Electrocardiol. 36, 69-74 (2003)) to evaluate the VT circuits associated with the individual infarct morphology and to predict the optimal targets of VT ablation in the given heart. This approach paves the way for a major paradigm shift in the clinical procedure of VT ablation, where identification of the optimal ablation targets in each individual heart would be carried out non-invasively by the present simulation methodology prior to the clinical procedure. Delivery of catheter ablation will then be minimally-invasive, swift and precise, eradicating all infarct-related VTs.

A mechanistic understanding of VT maintenance in infarcted hearts is presented, as well as how this new understanding allows for the accurate prediction, by means of computational modeling of arrhythmia in the individual heart, of the optimal targets of VT ablation. We then provide examples of the success of this "virtual EP lab" approach in accurately identifying the optimal ablation targets in a retrospective animal study.

Computational Modeling of Electrophysiology in Individual Ex-Vivo and In-Vivo Infarcted Hearts Ex-Vivo Heart Models. To understand the mechanisms maintaining VT in MI and how that knowledge can be used to determine the optimal targets of infarct-related VT ablation, we used a biophysically-detailed model of an individual canine heart with MI reconstructed from high-resolution ex-vivo MRI and diffusion tensor (DT)-MRI scans. FIGS. 1A-1C present the generation of the geometrical and structural aspects of the canine heart model. Infarcted tissue in the ventricles is discriminated from the rest of the myocardium, with the infarct further segmented out (FIG. 1A) into infarct scar and remodeled myocardium, the latter often referred to as border, peri-infarct, or gray zone (A. Schmidt, C. F. Azevedo, A. Cheng, S. N. Gupta, D. A. Bluemke, T. K. Foo, G. Gerstenblith, R. G. Weiss, E. Marban, G. F. Tomaselli, J. A. Lima, K. C. Wu, Infarct tissue heterogeneity by magnetic resonance imaging identifies enhanced cardiac arrhythmia susceptibility in patients with left ventricular dysfunction. *Circulation.* 115, 2006-2014 (2007)) based on the appearance of remodeled tissue in clinical MR images. Below we use the term gray zone (GZ). The resulting infarct segmentation shows strands of GZ tissue interdigitated with the electrically inert scar tissue, forming numerous channels within the scar.

Separation of the atria from the ventricles completes the geometric reconstruction of the model (FIG. 1B). Fiber orientation is based on DT-MRI data (FIG. 1C). A similar approach for ex-vivo MRI-based heart reconstruction has been used in our recent studies (J. D. Moreno, Z. I. Zhu, P. C. Yang, J. R. Bankston, M. T. Jeng, C. Kang, L. Wang, J. D. Bayer, D. J. Christini, N. A. Trayanova, C. M. Ripplinger, R. S. Kass, C. E. Clancy, A computational model to predict the effects of class I anti-arrhythmic drugs on ventricular rhythms *Sci. Transl. Med.* 3, 98ra83 (2011); K. S. McDowell, H. J. Arevalo, M. M. Maleckar, N. A. Trayanova, Susceptibility to arrhythmia in the infarcted heart depends on myofibroblast density *Biophys. J.* 101, 1307-1315 (2011); V. Gurev, T. Lee, J. Constantino, H. Arevalo, N. A. Trayanova, Models of cardiac electromechanics based on individual hearts imaging data: image-based electromechanical models of the heart *Biomech. Model. Mechanobiol.* 10, 295-306 (2011)).

The canine heart is characterized with an extensive GZ (P. Ursell, P. Gardner, A. Albala, J. F. Jr., A. Wit, Structural and electrophysiological changes in the epicardial border zone of myocardial infarcts during infarct healing. *Circ. Res.* 56, 436-452 (1985)), while infarcted swine (the animal model used to demonstrate the capabilities of our approach, see below) and human hearts have been shown to be arrhythmogenic with smaller GZs. To create cardiac geometrical models with the same infarct scar but with different (smaller) GZ volumes, the GZ was "morphologically eroded," decreasing GZ volume while preserving object topology.

In-Vivo Heart Models. To demonstrate that our simulation methodology can successfully predict the optimal ablation targets, we conducted a retrospective modeling study of infarct-related VT ablation in swine hearts. Models were generated from in-vivo MRI scans pre-ablation (FIG. 1D). To the best of our knowledge, this is the first development and application of heart models from in-vivo MRI. While the general electrophysiological model generation pipeline was similar to that for ex-vivo hearts, there were also significant differences. The first was in the segmentation process (FIG. 1D), where the ventricles were segmented by fitting cubic splines around manually identified landmark points demarcating the epicardial and endocardial surfaces; the full in-vivo geometrical model is shown in FIG. 1E. The second difference consisted in the fact that fiber orientation could not be acquired in this case. Therefore, fiber orientation was assigned in the in-vivo reconstructed hearts (FIG. 1F) using a novel geometry-driven approach (J. D. Bayer, R. Blake, G. Plank, Trayanova N, Novel rule based algorithm for assigning myocardial fiber orientation to computation heart models. *Ann Biomed Eng.*, (in submission) (2012)).

Assigning Electrophysiological Properties. The ex-vivo and in-vivo electrophysiological ventricular models were completed by assigning different electrophysiological properties to normal and GZ tissue; biophysically-detailed models of the action potentials (see Methods, below) in these regions are shown in FIG. 1G. Scar and ablation lesions were assumed electrically insulating.

The 3D Organizing Centers of Infarct-Related Monomorphic VT are Contained within the Infarct GZ Using the canine ex-vivo model (GZ volume=5.0 cm$^3$), we simulated programmed electrical stimulation (PES) delivered from 27 different endocardial sites. The PES protocol consisted of pacing at a cycle length of 300 ms for 6 beats followed by one or two premature extrastimuli delivered at shorter intervals until VT was induced, similar to protocols used in experimental studies (H. Ashikaga, T. Sasano, J. Dong, M. M. Zviman, R. Evers, B. Hopenfeld, V. Castro, R. H. Helm, T. Dickfeld, S. Nazarian, J. K. Donahue, R. D. Berger, H. Calkins, M. R. Abraham, E. Marban, A. C. Lardo, E. R. McVeigh, H. R. Halperin, Magnetic resonance-based anatomical analysis of scar-related ventricular tachycardia: implications for catheter ablation *Circ. Res.* 101, 939-947 (2007); T. Sasano, A. D. McDonald, K. Kikuchi, J. K. Donahue, Molecular ablation of ventricular tachycardia after myocardial infarction. 12, 1256-1258 (2006)). Monomorphic VT was induced in the model following PES from 8 out of the 27 pacing sites. VT persisted for the entire 2 s of simulated time interval. Pseudo-ECGs were calculated in all cases, as described in Methods.

Figures 2A, 2B, 2C:
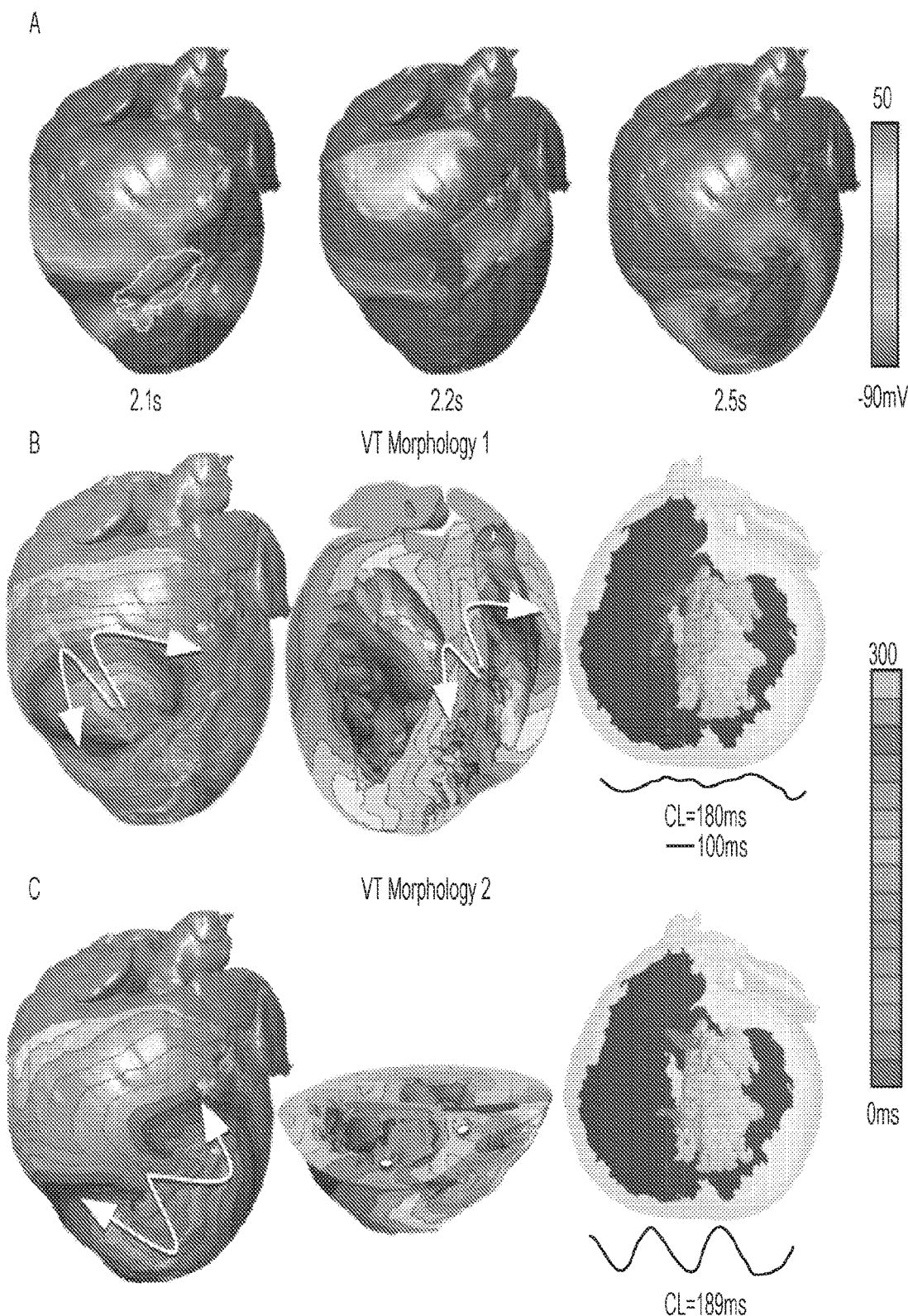
FIGS. 2A-2C show VT induction in the canine heart. A. Transmembrane potential maps during PES (GZ outlined in white). B. Activation map, VT morphology 1, demonstrating figure-of-eight reentry on the epicardium and RV endocardium. Reentry circuits are organized around two I-type filaments (pink lines) located within GZ with endpoints on the epicardium and RV endocardium. C. VT morphology 2, manifested as figure-of-eight reentry on epicardium and breakthroughs on endocardium (white dots). Reentry was organized around two I-type filaments with endpoints on the epicardium and scar.

For all VTs induced, reentry initiation took place within the GZ. FIG. 2A presents transmembrane potential maps depicting the events leading to reentry initiation for PES from the LV apex. The GZ exhibited slowed conduction and longer recovery time compared to the surrounding healthy tissue (FIG. 2A, 2.1s). This resulted in conduction block (FIG. 2A, 2.2s), wavebreak, and reentry formation (FIG. 2A, 2.5s). For all PES sites resulting in VT induction, the reentrant circuit was manifested as a figure-of-eight pattern on the epicardium.

VT morphologies induced from the eight pacing sites were not all unique. Comparison of pseudo-ECGs demonstrated two distinct VT morphologies. The first VT morphology resulted from PES at two sites, both on RV, and had an average cycle length of 190 ms. The reentrant circuit was a figure-of-eight pattern on the epicardium and RV endocardium (FIG. 2B). To gain further insight into the spatiotemporal organization of the VT circuit, the organizing centers of reentry (the filaments) were calculated (see Methods). For this VT morphology, the reentry revolved around two I-type filaments with endpoints at the epicardium and RV endocardium (FIG. 2B, pink lines). The filaments were fully contained within the GZ and the endpoints remained in the same locations for the duration of the VT.

The second VT morphology resulted from PES at six LV endocardial sites. The average cycle length, 222±17 ms, was longer than that of the first VT morphology. The figure-of-eight reentry on the epicardium had chirality opposite to that of the first VT morphology, and was manifested as breakthroughs on LV and RV endocardial surfaces (FIG. 2C). This was due to the reentrant activity being organized around two I-type filaments with endpoints at the epicardium and the infarct scar. Since the filaments did not extend to the endocardium, no rotational activity was observed there. Both filaments were stably located within the GZ throughout the VT duration.

Figures 3A, 3B, 3C:
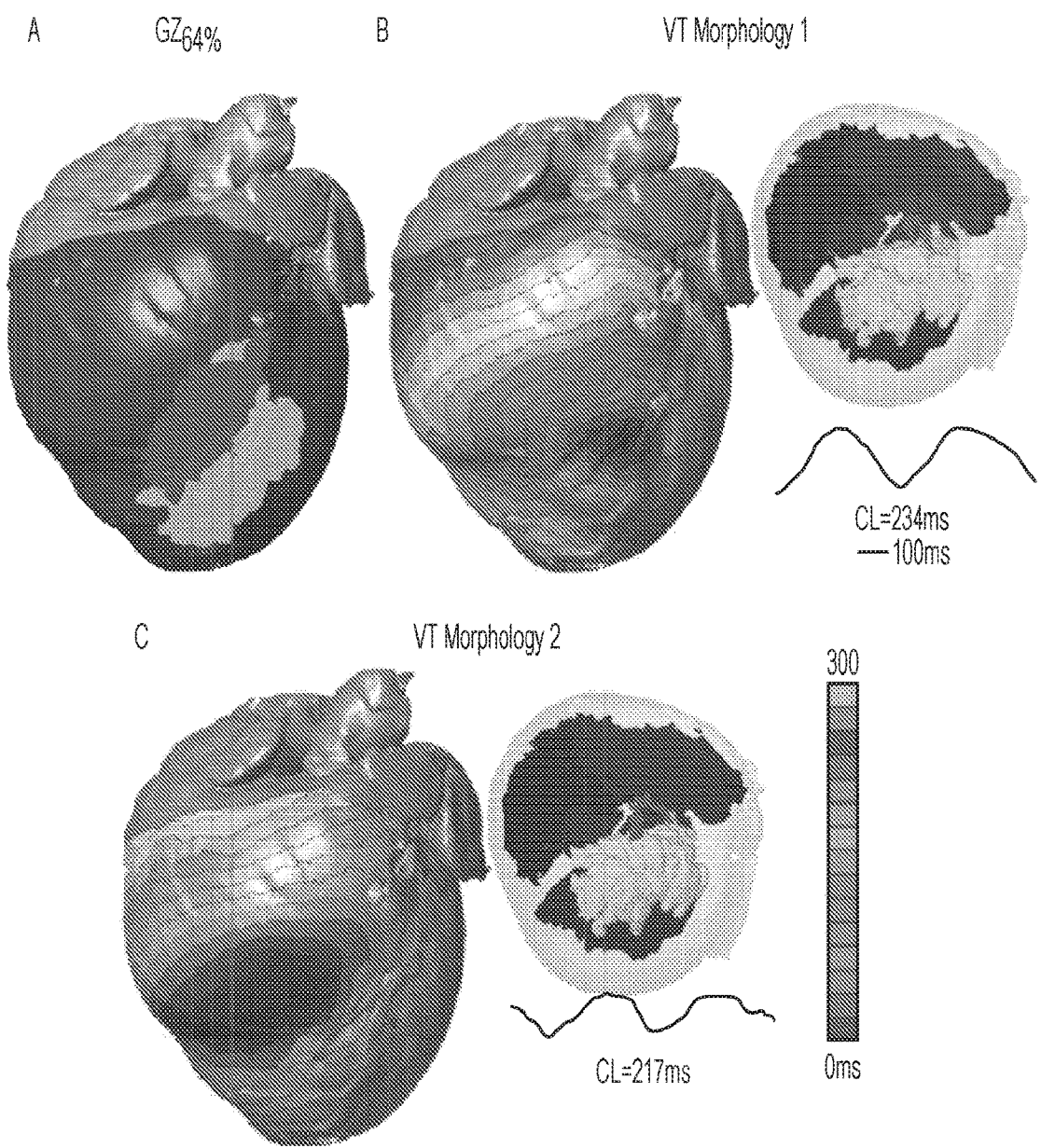
FIGS. 3A-3C show morphological erosion of GZ. A. Model with GZ volume 64% of the original. B. and C. Activation maps of the two VT morphologies induced after PES; both manifest as breakthrough on the epicardium and are organized around a U-type filament with endpoints on the scar.

Decreasing GZ volume by morphological erosion to values found in arrhythmogenic swine (K. H. Schuleri, M. Centola, R. T. George, L. C. Amado, K. S. Evers, K. Kitagawa, A. L. Vavere, R. Evers, J. M. Hare, C. Cox, E. R. McVeigh, J. A. C. Lima, A. C. Lardo, Characterization of Peri-Infarct Zone Heterogeneity by Contrast-Enhanced Multidetector Computed Tomography *J. Am. Coll. Cardiol.* 53, 1699 <last_page>1707 (2009)) or human hearts (A. Schmidt, C. F. Azevedo, A. Cheng, S. N. Gupta, D. A. Bluemke, T. K. Foo, G. Gerstenblith, R. G. Weiss, E. Marban, G. F. Tomaselli, J. A. Lima, K. C. Wu, Infarct tissue heterogeneity by magnetic resonance imaging identifies enhanced cardiac arrhythmia susceptibility in patients with left ventricular dysfunction. *Circulation.* 115, 2006-2014 (2007)) with MI resulted in the GZ becoming intramural and no longer extending to the epicardium as in the canine ventricles. In the model with GZ at 64% of the original volume (FIG. 3A, GZ=3.23 cm$^3$), PES from the same 27 endocardial sites induced 9 VTs (average cycle length 227±23 ms) with two distinct pseudo-ECG morphologies (FIGS. 3B-3C). For both VT morphologies, the VT manifested itself as a breakthrough on both endo- and epicardium (FIGS. 3B-3C), with a figure-of-eight intramural pattern. The reentrant activity was organized around a single U-type filament attached with both ends to the scar and fully contained within the GZ.

Further reduction of GZ to 37% of the original volume (1.88 cm$^3$) resulted in VT induction by PES from 7 sites with an average VT cycle length of 196±7 ms; all VTs had the same morphology. VT was similarly organized around a U-type filament located in its entirety within GZ, which remained stable for the duration of the simulation. Reentry was again intramural with breakthroughs on both epi- and endocardial surfaces.

Decreasing GZ Below Critical Size Results in VT Non-Inducibility

Further morphological erosion of GZ resulting in the critical GZ volume of 12.6% of the original (0.76 cm$^3$) resulted in inability to induce VT from any pacing site. In this case, the GZ volume was too small to support filament formation. No VT could be induced for any GZ volume below this critical value. These results indicate that there is a minimum GZ volume necessary to support filament formation in this heart.

The critical GZ volume obtained in our simulations is comparable to that reported in experiments. Using in-vivo Mill with late gadolinium enhancement (LGE) of pig hearts with MI, Estner et al (H. L. Estner, M. M. Zviman, D. Herzka, F. Miller, V. Castro, S. Nazarian, H. Ashikaga, Y. Dori, R. D. Berger, H. Calkins, A. C. Lardo, H. R. Halperin, The Critical Isthmus Sites of Ischemic Ventricular Tachycardia are in Zones of Tissue Heterogeneity, Visualized by Magnetic Resonance Imaging *Heart Rhythm.* (2011)) found that hearts with non-inducible VT had GZ volumes 13±5% of total infarct volume. These findings match ours: in the model where GZ volume was reduced to 12.6% of total infarct volume (the critical value of 0.76 cm,$^3$ as described above), VT was not inducible. Our simulations demonstrate that large GZ volumes were able to support a larger number of stable filaments, resulting in multiple VT morphologies arising from the same infarct geometry (FIGS. 2-3). Intermediate GZ volumes were able to support typically a single filament giving rise to the same VT morphology regardless of PES site, while GZ volumes below the critical value resulted in VT non-inducibility due to insufficient amount of electrically remodeled tissue to support reentrant activity.

Targeting of Filaments in the GZ for Optimal VT Ablation

The results presented above suggest that targeting GZ with catheter ablation to decrease its size and bring it below the critical volume for sustaining reentrant activity would result in successful termination of VT. This approach has recently been validated in a retrospective study that showed that successful ablation sites, as determined during standard electrophysiological study, co-localized with GZ (H. L. Estner, M. M. Zviman, D. Herzka, F. Miller, V. Castro, S. Nazarian, H. Ashikaga, Y. Dori, R. D. Berger, H. Calkins, A. C. Lardo, H. R. Halperin, The Critical Isthmus Sites of Ischemic Ventricular Tachycardia are in Zones of Tissue Heterogeneity, Visualized by Magnetic Resonance Imaging *Heart Rhythm.* (2011)). Results from recent clinical ablations studies have demonstrated a significant benefit from encircling the infarct scar with ablation lesions (J. M. Frapier, J. J. Hubaut, J. L. Pasquié, P. A. Chaptal, Large encircling cryoablation without mapping for ventricular tachycardia after anterior myocardial infarction: Long-term outcome *J. Thorac. Cardiovasc. Surg.* 116, 578 <last_page> 583 (1998); R. G. De Maria, M. Mukaddirov, P. Rouviere, E. Barbotte, B. Celton, B. Albat, J. Frapier, Long-Term Outcomes After Cryoablation for Ventricular Tachycardia During Surgical Treatment of Anterior Ventricular Aneurysms *Pacing and Clinical Electrophysiology.* 28, S168-171 (2005)). However, such an approach results in increased damage to functioning myocardium that could lead to depressed ventricular function (K. Soejima, M. Suzuki, W. H. Maisel, C. B. Brunckhorst, E. Delacretaz, L. Blier, S. Tung, H. Khan, W. G. Stevenson, Catheter ablation in patients with multiple and unstable ventricular tachycardias after myocardial infarction: short ablation lines guided by reentry circuit isthmuses and sinus rhythm mapping. *Circulation.* 104, 664-669 (2001); H. H. Khan, W. H. Maisel, C. Ho, M. Suzuki, K. Soejima, S. Solomon, W. G. Stevenson, Effect of radiofrequency catheter ablation of ventricular tachycardia on left ventricular function in patients with prior myocardial infarction *J. Interv. Card. Electrophysiol.* 7, 243-247 (2002)); current clinical guidelines encourage targeted approaches that minimize the ablation lesion (E. M. Aliot, W. G. Stevenson, J. M. Almendral-Garrote, F. Bogun, C. H. Calkins, E. Delacretaz, P. D. Bella, G. Hindricks, P. Jais, M. E. Josephson, J. Kautzner, G. N. Kay, K.-. Kuck, B. B. Lerman, F. Marchlinski, V. Reddy, M.-. Schalij, R. Schilling, K. Soejima, D. Wilber, EHRA/HRS Expert Consensus on Catheter Ablation of Ventricular Arrhythmias: Developed in a partnership with the European Heart Rhythm Association (EHRA), a Registered Branch of the European Society of Cardiology (ESC), and the Heart Rhythm Society (HRS); in collaboration with the American College of Cardiology (ACC) and the American Heart Association (AHA) *Europace*. 11, 771 <last_page>817 (2009; 2009)).

Based on the new mechanistic insight regarding VT maintenance in the zone of infarct, and specifically, the fact that the scroll-wave filaments were anchored in specific regions of the GZ while being fully contained within the GZ, as described above, we hypothesized that ablating GZ region(s) containing the scroll wave filament(s) would terminate all VTs. To test this hypothesis, ablation lesions that encompass the scroll-wave filaments were implemented in all models with different GZ volumes; the lesions were assumed electrically inactive.

Figures 4A, 4B:
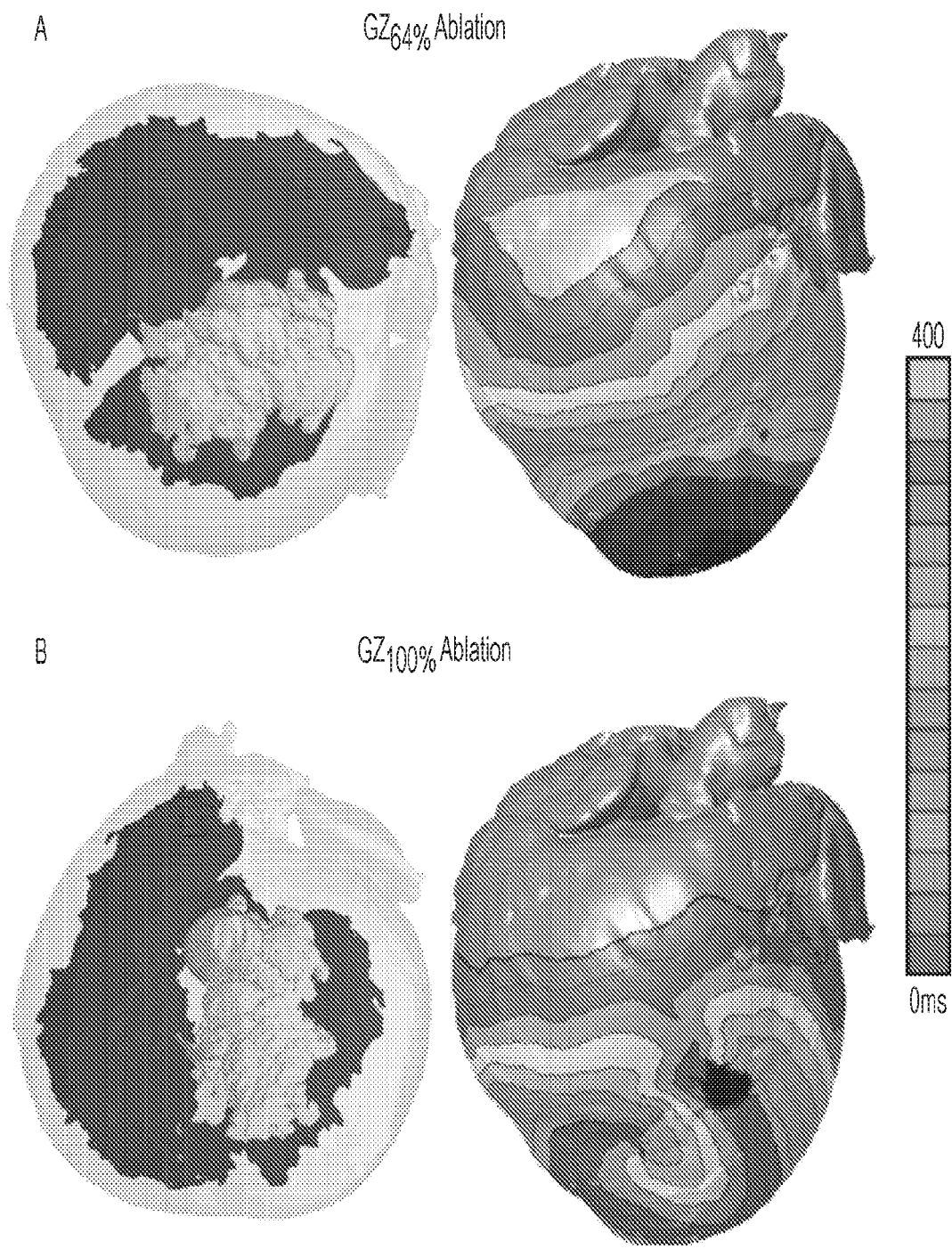
FIGS. 4A and 4B show targeting filaments for ablation. A. Ablating the site of U-type filament formation shown in FIG. 3B-3C results in VT non-inducibility. B. Ablating only one of I-type filaments shown in FIG. 2C results in ablation failure. The resulting reentry is organized around a different I-type filament with endpoints on epicardium and scar.

FIG. 4A presents ablation of the tissue in which the U-shaped scroll-wave filament sustaining each of the VTs shown in FIGS. 3B-3C was formed. Model ablation was successful and VT could no longer be induced by PES from any of the 27 sites (FIG. 4A). Similar was the outcome of ablation in the other models (different GZ volume) where VT was sustained by a single U-shaped filament (not shown here). Importantly, while the ablation in FIG. 4A decreased GZ volume (to 2.84 cm$^3$), it did not bring it below the critical level for which VT can no longer be initiated (0.76 cm$^3$). Thus, targeting the scroll-wave filaments sustaining VT, all of which are contained within GZ, is the most effective way of terminating infarct-related VT. Ablating the tissue in which the two I-shaped scroll wave filaments sustaining the VTs in FIG. 2 resided also resulted in VT non-inducibility. The larger GZ (and thus longer filaments) required more extensive ablation lesions to encompass the filaments.

FIG. 4B shows ablation of only one of the two filaments sustaining reentry in FIG. 2, resulting in failure to terminate all VTs. Following ablation, the modified morphology and size of the GZ resulted in VT being sustained by a different I-type filament, with ends attached to the scar and epicardium.

The simulations described above demonstrate that accurate identification of the optimal ablation targets in each individual heart could be carried out by determining, by means of individual MRI-based heart modeling, the locations of all scroll-wave filaments that sustain VT in the particular MI heart. Ablating the tissue in which the filaments resided successfully terminates all VTs. The simulation results also demonstrate that even when the first ablation attempt could be unsuccessful (because of, for instance, the filaments being difficult to fully access by an endo- or epicardial catheter approach in the EP lab), the new ablation targets (new filaments) associated with the modified VT substrate (modified GZ morphology and size) can be calculated again from the model, providing a dynamic update of the optimal ablation targets.

Sensitivity of VT Filaments to GZ Model Parameters

The simulation results described above clearly demonstrate the paramount role that the GZ plays in establishing the locations, number and type of the scroll-wave filament(s) that sustain monomorphic VT in the MI heart. Since the filaments are the optimal ablation targets, accurate identification of their spatial positioning in each individual heart is key to the clinical translation of this simulation-guidance-of-VT-ablation approach. In the models presented here, GZ is represented as a homogenous region characterized with average electrophysiological remodeling (homogenous changes in ionic currents and conductivities, the latter resulting from Cx43 downregulation and lateralization). However, histological examinations of infarcted tissue have shown that voxels identified as GZ from MR scans correspond to microscopically heterogeneous mixtures of viable myocardium and infarct scar (H. Arheden, M. Saeed, C. B. Higgins, D. W. Gao, P. C. Ursell, J. Bremerich, R. Wyttenbach, M. W. Dae, M. F. Wendland, Reperfused rat myocardium subjected to various durations of ischemia: estimation of the distribution volume of contrast material with echo-planar MR imaging *Radiology*. 215, 520-528 (2000)). Representing GZ as a heterogeneous region would significantly complicate the model. Most importantly, the degree of GZ heterogeneity is difficult to assess from MRI scans, which would render the clinical utility of the simulation guidance approach to VT ablation difficult to ascertain. Therefore, we performed simulations to determine the sensitivity of the spatial position of the VT filaments to the degree of GZ structural heterogeneity.

Similarly, we represent the ionic current remodeling in the GZ as a set of homogeneous ion current conductance changes, with specific data derived from the extensive literature on the canine epicardial border zone properties, as described in Methods. However, ionic current downregulation could be different in different animal species and the human, and data may not be readily available; furthermore, there could be significant variability in GZ ionic current remodeling between individual hearts. Demonstrating that physiological variations in GZ ionic current remodeling do not affect the accurate prediction of scroll-wave filaments by our modeling approach makes the clinical translation of the approach feasible because it eliminates the need to obtain information about the GZ electrophysological properties in each individual heart. Therefore, we also performed simulations to determine the sensitivity of the spatial position of the VT filaments to the degree of ionic current remodeling in the GZ.

In both sets of simulations, we deemed the spatial position of the VT filaments not sensitive to a particular set of GZ model parameters when this position remained within the approximate volume of a single clinical ablation lesion. As shown by Lardo et al (A. C. Lardo, E. R. McVeigh, P. Jumrussirikul, R. D. Berger, H. Calkins, J. Lima, H. R. Halperin, Visualization and temporal/spatial characterization of cardiac radiofrequency ablation lesions using magnetic resonance imaging *Circulation*. 102, 698-705 (2000)), the size of a typical single ablation lesion is 9.4±0.05 mm by 6.7±0.05 mm by 3.4±2.1 mm.

Figures 5A, 5B, 5C, 5D, 5E, 5F:
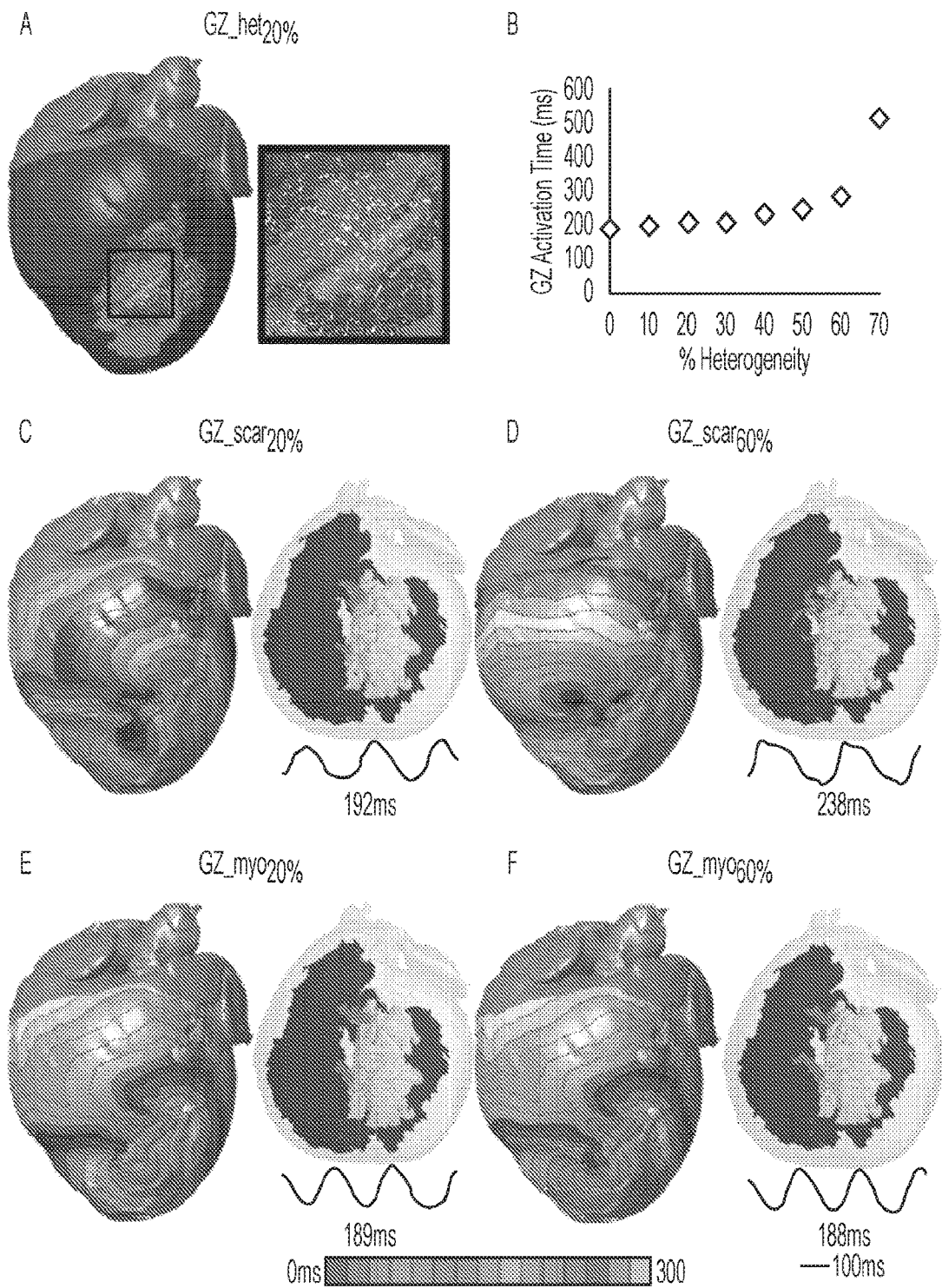
FIGS. 5A-5F show sensitivity of filament position to GZ electrophysiological properties. A. Model with 20% scar in GZ (white speckles). B. Time needed to fully activate GZ as a function of scar density in GZ. C. and D. Activation maps, filaments, and pseudo-ECGs for GZs composed of 20% and 60% scar. E. and F. Same for GZ composed of 20% and 60% normal myocardium.

In the first set of simulations, micro-regions of scar were randomly distributed in the models throughout the GZ volume at varying densities (10% to 90% of GZ volume in 10% steps, FIG. 5A shows the 20% case), although histological studies have demonstrated that scar infiltration in the GZ is only up to 40% of GZ volume (H. Arheden, M. Saeed, C. B. Higgins, D. W. Gao, P. C. Ursell, J. Bremerich, R. Wyttenbach, M. W. Dae, M. F. Wendland, Reperfused rat myocardium subjected to various durations of ischemia: estimation of the distribution volume of contrast material with echo-planar MR imaging *Radiology*. 215, 520-528 (2000)). Following PES, the locations of the resulting filaments were compared to those in the corresponding homogeneous GZ model. Incorporation of scar in the GZ resulted in conduction slowing within GZ. The total time it took to fully activate the GZ increased with increased degree of scar density (FIG. 5B). For the heterogeneous cases with GZ composed of up to 40% scar, all induced VT morphologies were identical to that in control (FIG. 2B). FIG. 5C shows the activation maps and filament locations for the model that incorporated 20% scar in the GZ. VT cycle length was 2% longer than in control, with VT again manifested as a figure-of-eight reentry on the epicardium and breakthrough on the endocardium. Most importantly, the filaments remained in the same spatial position, with accuracy fully within one clinical lesion.

As GZ scar density increased to more than 70%, wavefronts did not fully propagate through GZ, rendering it functionally identical to the scar; VT was also not inducible. In FIG. 5D (60% scar), VT cycle length was 26% longer than in control. The VT was manifested as 6 reentries on the epicardium, with multiple filaments densely packed within the GZ. Despite the more complex VT spatiotemporal dynamics, filaments remained within the same general area as in control.

In the second set of simulations, we similarly incorporated random micro-regions in the GZ at increasing density, this time composed of normal myocardium. The simulations revealed that models with unchanged GZ conductivities but GZ composition incorporating up to 80% normal tissue exhibited the same VT morphology as in control; VT cycle lengths also did not differ significantly from the control (188.1±0.76 ms). Increasing the amount of GZ normal tissue to 90% and 100% rendered VTs non-inducible. FIGS. 5E-5F show the activation maps and filament locations for the VTs induced in models with 20% and 60% normal tissue in GZ. In both cases, there were slight changes in the activation pattern within the GZ as compared to control, but the reentrant patterns remained the same. Again, the filaments remained in the same spatial position, with accuracy within one clinical lesion.

These simulations demonstrate that scroll-wave filament locations are not particularly sensitive to the composition of the GZ and are determined predominately by GZ morphology and size. The results also strengthen significantly the possibility of clinical translation of the proposed "virtual EP lab" approach for identifying the optimal VT ablation targets since they demonstrate that the approach needs only the acquisition of the clinical MR and a model with "average" electrophysiological properties.

Predicting the Optimal Ablation Targets: A Retrospective Animal Study

To demonstrate that our modeling approach can successfully be used to predict the optimal ablation targets, we conducted a retrospective animal study. Five pigs underwent intracardiac electrophysiological (EP) study to ablate post-MI VT; in-vivo MRIs with LGE pre- and post-ablation were also acquired (see Methods). Of the five hearts, ablation succeeded and VT was non-inducible during a follow up EP study 1 week post-ablation; in the other 3, ablation failed. All swine hearts were reconstructed from the in-vivo MIl scans, ventricular electrophysiological models created, and PES simulated to determine arrhythmogenicity, VT morphology, and filament locations.

Figures 6A, 6B, 6C, 6D, 6E, 6F:
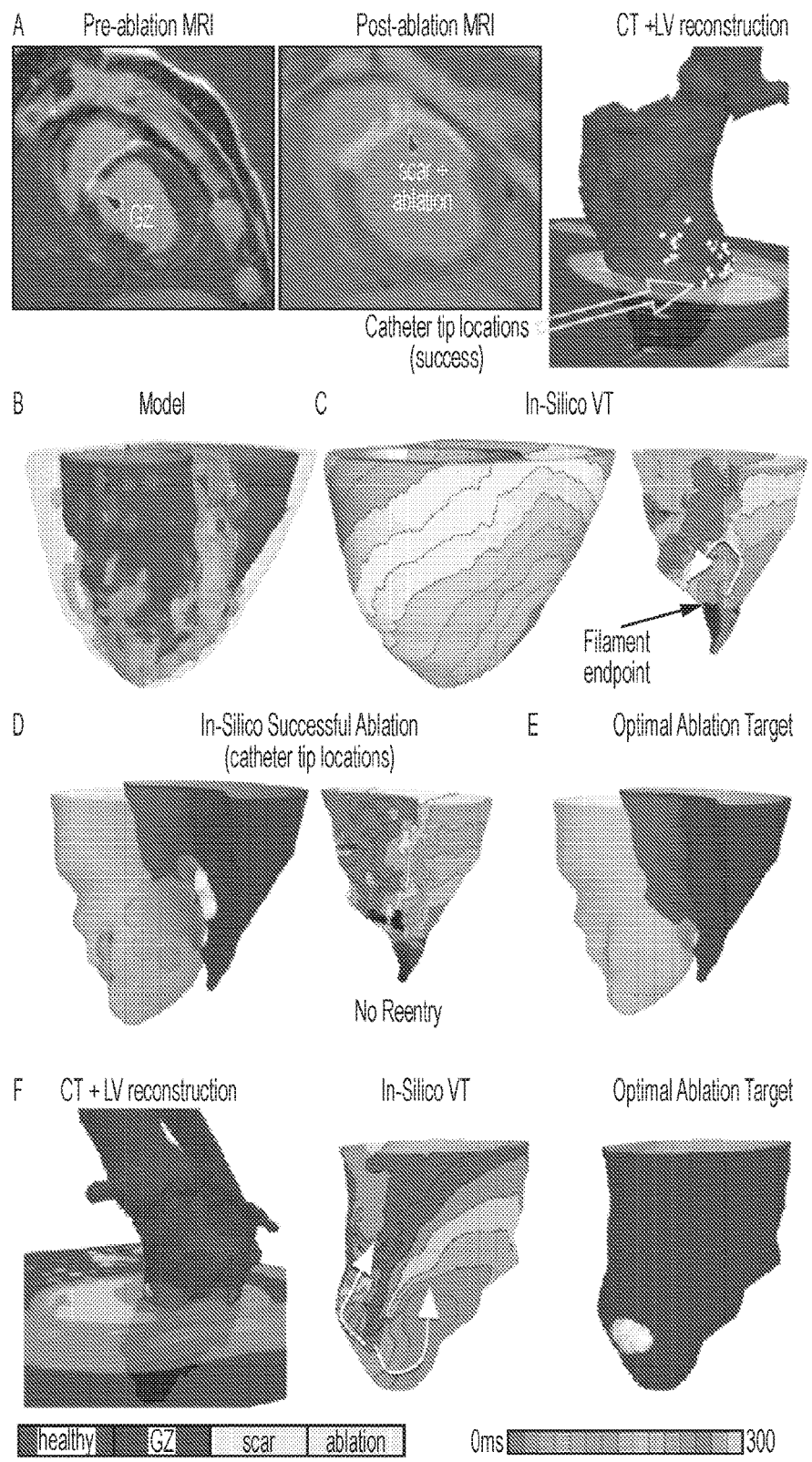
FIGS. 6A-6F show retrospective validation of successful ablation in swine hearts according to an embodiment of the current invention. A. Pre- and post-ablation in-vivo MRI; reconstruction of LV endocardium from CT (rendered semi-transparently) with the locations of catheter tip (white dots). B. Model reconstructed from pre-ablation MRI (epicardium and GZ rendered semi-transparent). C. Simulated VT activation map, with reentry organized around a filament with endpoints on the RV side of septum and scar. D. Incorporating experimental ablation in the model also results in VT non-inducibility. E. Targeted ablation of the filament renders VT non-inducible. F. Another example of heart with successful VT ablation. Corresponding VT simulation and predicted optimal ablation target are also shown.

FIG. 6 presents experimental and simulation results for the two hearts where post-MI VT was chronically ablated. FIG. 6A shows pre- and post-ablation MRIs of one pig heart, as well as the LV endocardium reconstructed from CT with the locations of the catheter tip delivering ablation (white dots) registered on the endocardial surface. In this heart, lesions were created throughout the septum, successfully terminating VT. Comparing pre- and post-ablation MRIs demonstrated that the ablated region co-localized with the GZ in the septum (FIG. 6A). The computational model accurately reconstructed the septal infarct with islands of viable GZ (FIG. 6B). Following PES, the induced VT organized around an I-type filament located on the septum with endpoints on the RV endocardium and scar (FIG. 6C). Implementing in the model the experimental lesions also successfully terminated VT (FIG. 6D), demonstrating excellent correspondence between model and experiment. However, the experimental ablation lesions were fairly extensive (FIG. 6D). The simulations demonstrated that a smaller ablation lesion at the location of the filament would have successfully terminated VT (FIG. 6E).

FIG. 6F shows another example of excellent correspondence between experiment and simulation prediction. In this animal, ablation delivered at a relatively small area on the septum chronically rendered VT non-inducible. The simulations revealed that the presence of GZ in this area resulted in the formation of two I-type filaments; thus this region was the optimal ablation target.

Figures 7A, 7B, 7C, 7D, 7E, 7F:
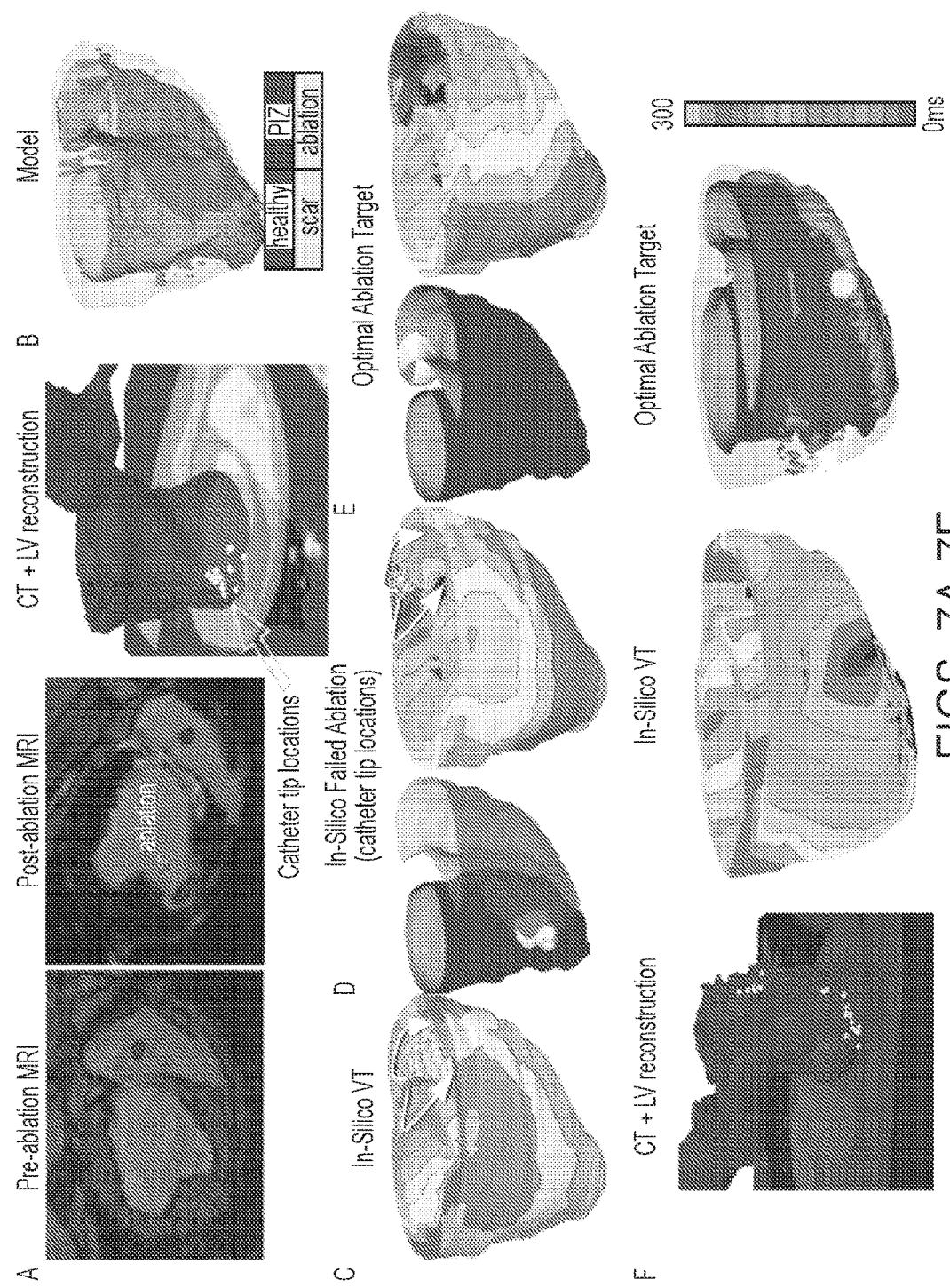
FIGS. 7A-7F show retrospective validation of failed ablation in swine hearts. A. Pre- and post-ablation in-vivo MRI; reconstruction of LV endocardium from CT. B. Model reconstruction (epi- and endocardium rendered semi-transparent). C. Simulated VT activation map, with reentry figure-of-eight reentry on anterior RV. D. Incorporating experimental ablation in the model also results in ablation failure. E. Simulation-predicted optimal ablation target. F. Another example of heart with failed ablation with corresponding simulated MI-related VT and predicted optimal ablation target.

For the three animals where VT was not chronically ablated, the post-ablation MRI revealed that ablation was not delivered at the GZ. FIG. 7A shows that in one animal the heart was ablated along the posterior portion of the LV wall near the RV insertion point. MRI with LGE post-ablation revealed that the lesions were distal from the infarct, the latter located primarily at the septum and anterior portion of the LV (FIG. 7A). Using the pre-ablation reconstruction shown in FIG. 7B and simulating PES revealed that reentry was organized around two I-type filaments in the GZ located at the anterior portion of the RV (FIG. 7C). Simulations that incorporated the experimental ablation lesions correctly predicted that VT would remain inducible (FIG. 7D), with morphology similar to pre-ablation. Ablating the site of filament formation at the GZ in the RV resulted in ablation success in-silico (FIG. 7E).

FIG. 7F shows another example where experimental ablation was delivered at sites distal from the GZ. In this case, the heart was ablated at the anterior LV wall near the RV insertion point and the LV free wall near the base. The simulations correctly predicted VT termination failure when the experimental lesions were incorporated in the model. Modeling was able to determine that GZ in RV harbored the filaments and was the optimal ablation target. Similar was the case of failed ablation in the third pig (results not shown).

Discussion

Ventricular ablation is currently offered to MI patients with recurrent infarct-related VT. A catheter is inserted through veins for an endocardial approach to map the electrical activity of the heart following an arrhythmia induction protocol, so that the targets of ablation can be identified (E. M. Aliot, W. G. Stevenson, J. M. Almendral-Garrote, F. Bogun, C. H. Calkins, E. Delacretaz, P. D. Bella, G. Hindricks, P. Jais, M. E. Josephson, J. Kautzner, G. N. Kay, K.-. Kuck, B. B. Lerman, F. Marchlinski, V. Reddy, M.-. Schalij, R. Schilling, K. Soejima, D. Wilber, EHRA/HRS Expert Consensus on Catheter Ablation of Ventricular Arrhythmias: Developed in a partnership with the European Heart Rhythm Association (EHRA), a Registered Branch of the European Society of Cardiology (ESC), and the Heart Rhythm Society (HRS); in collaboration with the American College of Cardiology (ACC) and the American Heart Association (AHA) *Europace.* 11, 771 <last_page>817 (2009; 2009)). Mapping is a meticulous process, lasting for several hours, in which information regarding the electrical activity on the ventricular surface is collected from the tip of a roving catheter on a point-by-point basis (J. Brugada, A. Berruezo, A. Cuesta, J. Osca, E. Chueca, X. Fosch, L. Wayar, L. Mont, Nonsurgical transthoracic epicardial radiofrequency ablation: an alternative in incessant ventricular tachycardia. *J. Am. Coll. Cardiol.* 41, 2036-2043 (2003); E. Sosa, M. Scanavacca, A. d'Avila, F. Oliveira, J. A. Ramires, Nonsurgical transthoracic epicardial catheter ablation to treat recurrent ventricular tachycardia occurring late after myocardial infarction. *J. Am. Coll. Cardiol.* 35, 1442-1449 (2000)). The generated maps are thus typically of low resolution, and the propagation pathways, as identified from the maps, are only surface manifestations of the 3D reentrant circuits during infarct-related VT. Furthermore, mapping is best performed during sustained VT. However, patients often exhibit a hemodynamic intolerance to the sustained VT induced in the EP lab, which does not allow the time needed for detailed mapping. Therefore, infarct-related VT ablation remains a relatively high-risk procedure with a success rate far from desired (D. J. Callans, E. Zado, B. H. Sarter, D. Schwartzman, C. D. Gottlieb, F. E. Marchlinski, Efficacy of radiofrequency catheter ablation for ventricular tachycardia in healed myocardial infarction. *Am. J. Cardiol.* 82, 429-432 (1998)).

The above examples demonstrate some concepts of a non-invasive approach to identify the optimal infarct-related VT ablation targets according to an embodiment of the current invention. This embodiment includes using, prior to the clinical procedure, an MRI-based subject-specific multiscale electrophysiological model of the heart to analyze post-MI VT circuits and to determine the optimal ablation targets. The approach allows for a full 3D visualization and analysis of these circuits. As the results of the present study demonstrate, the optimal ablation targets are the scroll-wave filaments that sustain VTs, which were found to be stably located in the GZ. Once the optimal ablation targets are determined and visualized by the present approach, ablation delivery could be swift and precise, eradicating, with a minimal number of lesions, all infarct-related VTs. This will dramatically improve the efficacy of ablation, increase the tolerance for the procedure, and reduce post-procedure complications and long-term deleterious effects resulting from the lengthy invasive mapping and the numerous unnecessary ablation lesions. Translating the approach presented here into the clinic will constitute a dramatic shift in the paradigm of infarct-related VT ablation procedure.

Importantly, the approach presented here allows for careful ablation procedure planning. It is possible that the locations of the scroll-wave filaments are not accessible, in their entirety, by any clinical endo- or epicardial approach. The subject-specific heart model could then be used to play out scenarios of tiered ablation approaches, where the filament locations are re-calculated following an initial model ablation that does not eradicate all filaments, much like in FIG. 4B. Such targeted "filament modification" approach (electrophysiologically equivalent to a targeted GZ substrate modification) in situations of restricted access to the sites will still terminate all VTs with a minimum number of ablation lesions.

The predictive capabilities of the approach were tested here in a retrospective animal study. We demonstrated that when the experimental lesions resulting in VT termination were implemented in the model, the latter also predicted VT termination; similarly, failed ablation in the experiment was also a failure to ablate VT in the model. Importantly, comparisons between experimental ablation lesions that eradicated VT and the optimal ablation lesions predicted by the model revealed that ablation could have succeeded with a much smaller number of ablations and an overall lesion size that is dramatically smaller than the one delivered in the experiment (FIG. 6).

A novel mechanistic insight from the results presented is that the scroll-wave filaments sustaining infarct-related monomorphic VT (i.e. the optimal ablation targets) are fully contained within the GZ; the simulation results also provided information regarding how GZ size determines filament type. GZ was thus the arrhythmogenic substrate that promoted wavebreak and reentry formation. Our findings are consistent with observations of epicardial reentrant activity anchored to regions of slow conduction within GZ, made during electrical mapping of post-MI VT (H. Ashikaga, T. Sasano, J. Dong, M. M. Zviman, R. Evers, B. Hopenfeld, V. Castro, R. H. Helm, T. Dickfeld, S. Nazarian, J. K. Donahue, R. D. Berger, H. Calkins, M. R. Abraham, E. Marban, A. C. Lardo, E. R. McVeigh, H. R. Halperin, Magnetic resonance-based anatomical analysis of scar-related ventricular tachycardia: implications for catheter ablation *Circ. Res.* 101, 939-947 (2007)). Similarly, recent clinical studies using contrast-enhanced cardiac Mill have shown that GZ extent correlates with arrhythmia susceptibility in patients with ischemic cardiomyopathy (A. Schmidt, C. F. Azevedo, A. Cheng, S. N. Gupta, D. A. Bluemke, T. K. Foo, G. Gerstenblith, R. G. Weiss, E. Marban, G. F. Tomaselli, J. A. Lima, K. C. Wu, Infarct tissue heterogeneity by magnetic resonance imaging identifies enhanced cardiac arrhythmia susceptibility in patients with left ventricular dysfunction. *Circulation.* 115, 2006-2014 (2007); A. T. Yan, A. J. Shayne, K. A. Brown, S. N. Gupta, C. W. Chan, T. M. Luu, M. F. Di Carli, H. G. Reynolds, W. G. Stevenson, R. Y. Kwong, Characterization of the peri-infarct zone by contrast-enhanced cardiac magnetic resonance imaging is a powerful predictor of post-myocardial infarction mortality. *Circulation.* 114, 32-39 (2006); S. D. Roes, C. J. Borleffs, R. J. van der Geest, J. J. Westenberg, N. A. Marsan, T. A. Kaandorp, J. H. Reiber, K. Zeppenfeld, H. J. Lamb, A. de Roos, M. J. Schalij, J. J. Bax, Infarct tissue heterogeneity assessed with contrast-enhanced Mill predicts spontaneous ventricular arrhythmia in patients with ischemic cardiomyopathy and implantable cardioverter-defibrillator *Circ. Cardiovasc. Imaging.* 2, 183-190 (2009)). The filament locations in GZ were found to not be sensitive to the structural composition of the GZ. Our simulations show that the presence of up to 40% of scar in GZ does not affect filament spatial position; even with 70% scar in GZ, the induced VTs still had filaments located in approximately the same general region as in the model without scar tissue in GZ (FIGS. 5C-5D). The filaments spatial position was also not much sensitive to the degree of ionic current remodeling in GZ. For a given PES site, GZ morphology and size were found to be the main determinants of filament number, location, and type. Our simulations demonstrated that approximating the GZ as a homogeneously remodeled tissue with slowed conduction is sufficient to predict the locations of post-MI VT filaments.

The "virtual EP lab" presented here incorporates advanced image-processing for in-vivo MRI-based subject-specific heart model generation as well as sophisticated numerical simulation and analysis approaches. Should the methodology be successfully implemented in the clinic, it will constitute a major leap forward in the integration of computational modeling, traditionally a basic-science discipline, in the diagnosis and treatment of cardiac disease.

In conclusion, we presented examples of a novel approach for accurate identification of infarct-related VT ablation targets according to an embodiment of the current invention. In this example, we focused on monomorphic VT, and demonstrated the predictive capabilities of the approach in a retrospective animal study.

Methods

Datasets and Model Creation

Ex-Vivo Canine Heart: Details regarding the image acquisition and reconstruction of the infarcted canine heart from ex-vivo MRI and DTMRI images were fully described elsewhere (F. Vadakkumpadan, H. Arevalo, A. J. Prassl, J. Chen, F. Kickinger, P. Kohl, G. Plank, N. Trayanova, Image-based models of cardiac structure in health and disease *Wiley Interdisciplinary Reviews: Systems Biology and Medicine.* 2, 489-506 (2010)).

In-Vivo Swine Hearts: The infarcted swine hearts imaging and EP study were previously described (H. L. Estner, M. M. Zviman, D. Herzka, F. Miller, V. Castro, S. Nazarian, H. Ashikaga, Y. Dori, R. D. Berger, H. Calkins, A. C. Lardo, H. R. Halperin, The Critical Isthmus Sites of Ischemic Ventricular Tachycardia are in Zones of Tissue Heterogeneity, Visualized by Magnetic Resonance Imaging *Heart Rhythm.* (2011) (H. L. Estner, M. M. Zviman, D. Herzka, F. Miller, V. Castro, S. Nazarian, H. Ashikaga, Y. Dori, R. D. Berger, H. Calkins, A. C. Lardo, H. R. Halperin, The Critical Isthmus Sites of Ischemic Ventricular Tachycardia are in Zones of Tissue Heterogeneity, Visualized by Magnetic Resonance Imaging *Heart Rhythm.* (2011)). For this example, we used a subset of the datasets (5 pigs) to prospectively validate our simulation methodology. In these pigs, MI was induced via occlusion of the mid-left anterior descending coronary artery. Four weeks after MI induction, the animals underwent in-vivo contrast-enhanced MRI at a resolution of 976×976×4000 µm$^3$. One day post-MRI, the animals underwent a full EP study to ablate VT. 7-9 days post-ablation, the animals underwent a follow up EP study to determine if ablation resulted in VT non-inducibility. A post-ablation in-vivo MRI was also performed.

FIGS. 1D-1F illustrate the reconstruction of hearts from pre-ablation in-vivo MRI. First, ventricles were segmented from the rest of the torso by fitting closed splines through a set of landmark points placed manually along the epi- and endocardial boundaries (FIG. 1D). These splines were then tricubically interpolated to obtain a segmentation of the ventricles with a resolution of 400×400×400 um$^3$. To segment the infarct, the MR images were tricubically interpolated to the same resolution as the ventricular segmentation. Gray-level thresholding was used to segment healthy myocardium, infarct scar, and GZ (A. Schmidt, C. F. Azevedo, A. Cheng, S. N. Gupta, D. A. Bluemke, T. K. Foo, G. Gerstenblith, R. G. Weiss, E. Marban, G. F. Tomaselli, J. A. Lima, K. C. Wu, Infarct tissue heterogeneity by magnetic resonance imaging identifies enhanced cardiac arrhythmia susceptibility in patients with left ventricular dysfunction. *Circulation.* 115, 2006-2014 (2007)). We used software tools developed by our group to create finite element meshes of the hearts that incorporated adaptive element sizing that preserves fine details of the geometry including infarct surfaces.

Electrophysiological Parameters: In healthy ventricular myocardium, passive electrical properties were defined using normal conductivity values (L. Clerc, Directional differences of impulse spread in trabecular muscle from mammalian heart. *J. Physiol. (Lond.).* 255, 335-346 (1976)) and ionic kinetics were described by the Luo-Rudy II model of ventricular action potential (C. Luo, Y. Rudy, A dynamic model of the cardiac ventricular action potential. II. Afterdepolarizations, triggered activity, and potentiation. *Circ Res.* 74, 1097-1113 (1994)) (FIG. 1G). The GZ incorporated experimentally determined changes that resulted in decreased transverse conductivity (J. Yao, W. Hussain, P. Patel, N. Peters, P. Boyden, A. Wit, Remodeling of gap junctional channel function in epicardial border zone of healing canine infarcts. *Circ. Res.* 92, 437-443 (2003)) and action potential with decreased excitability and increased duration (J. Pu, P. Boyden, Alterations of Na$^+$ currents in myocytes from epicardial border zone of the infarcted heart. A possible ionic mechanism for reduced excitability and postrepolarization refractoriness. *Circ. Res.* 81, 110-119 (1997); W. Dun, S. Baba, T. Yagi, P. A. Boyden, Dynamic remodeling of K+ and Ca2+ currents in cells that survived in the epicardial border zone of canine healed infarcted heart. *Am. J. Physiol. Heart Circ. Physiol.* 287, H1046-54 (2004); M. Jiang, C. Cabo, J. Yao, P. Boyden, G. Tseng, Delayed rectifier K currents have reduced amplitudes and altered kinetics in myocytes from infarcted canine ventricle. *Cardiovasc. Res.* 48, 34-43 (2000)).

Simulation Protocol and Analysis

Mathematical description of cardiac tissue was based on monodomain equations. The software CARP was used to solve this system of equations on a parallel computing system (E. Vigmond, M. Hughes, G. Plank, L. J. Leon, Computational tools for modeling electrical activity in cardiac tissue. *J. Electrocardiol.* 36, 69-74 (2003)).

To classify the induced VT morphologies, pseudo-ECGs were calculated by taking the difference of extracellular potentials between two points separated by 18 cm in an isotropic bath surrounding the hearts. The extracellular potentials were approximated using an integral equation by Gima et al (K. Gima, Y. Rudy, Ionic Current Basis of Electrocardiographic Waveforms: A Model Study. *Circ Res.* 90, 889-896 (2002)).

Scroll-wave filaments were determined by converting transmembrane potential maps into phase angle maps, and then determining the nodes where the integral of the phase angles of surrounding nodes was ±2π (C. Larson, L. Dragnev, N. Trayanova, Analysis of electrically-induced reentrant circuits in a sheet of myocardium. *Ann Biomed Eng.* 31, 768-80 (2003)). These nodes correspond to locations of phase singularities, which are the filament building blocks.

Some other aspects of the current invention are directed computational models of ventricular electromechanics in providing a new level of understanding of the relationship between electrical and mechanical activation in the heart, and how this understanding can be utilized to provide improved cardiac resynchronization therapy (CRT) strategies.

Dyssynchronous Heart Failure

Heart failure is a major cardiovascular disease affecting 5 million people in the US alone, and is associated with high morbidity and mortality rates (Lloyd-Jones et al., 2009). (The references cited in the following examples are listed below for convenience.) The syndrome is characterized with impaired pump function due to the deleterious remodeling of the ventricles, from the organ down to the molecular level, which significantly alters the electrical and mechanical behavior of the heart. High-resolution magnetic resonance imaging (MRI) and diffusion tensor (DT) MRI scans (Helm et al., 2006) have shown that in dyssynchronous heart failure (DHF) there is a substantial remodeling of ventricular geometry and structure. At the organ level, the ventricles become dilated and wall thickness is reduced. At the tissue level, laminar sheet angle is altered, and the transmural gradient in fiber orientation is increased. Because chamber geometry and sheet structure are major determinants of LV mechanics (Cheng et al., 2008; LeGrice et al., 1995), the mechanical deformation of the failing heart is markedly different. Furthermore, altered heart geometry as well as fiber and sheet orientations directly affect 3D electrical propagation (Hooks et al., 2007) in the failing heart.

Heart failure is also characterized with remodeling of the electrophysiological and mechanical properties at the cellular and subcellular levels. Studies (Akar et al., 2007; Akar et al., 2004) have shown that the gap junctional protein connexin43 (Cx43) is redistributed from the intercalated disk to the lateral myocyte borders and that the amount of hypophosphorylated Cx43 is increased, leading to reduced conduction velocity in heart failure. There is a considerable downregulation of the membrane potassium channels carrying the Ito and IK1 currents (Kaab et al., 1996) and of the intracellular Ca2+ATPase (SERCA) pump (O'Rourke et al., 1999), and upregulation of the Na—Ca exchanger (NCX) (O'Rourke et al., 1999). Remodeled ionic currents and Ca2+ handling result in altered Ca2+ transients, which, in turn, impair active tension development by the myofilaments in the cell. Finally, differential expression of collagen isoforms (Marijianowski et al., 1995) and altered ratio of titin (Wu et al., 2002) (an intrasarcomeric protein that modulates myofilament passive tension) isoforms results in increased myocardial stiffness.

Because of the combined effects of chamber, contractile, and electrophysiological remodeling, the ability of the LV to efficiently pump blood is severely compromised in heart failure patients. Furthermore, a subset of these patients exhibits abnormal electrical conduction that delays activation of one portion of the ventricle relative to another (intraventricular conduction delay due to left bundle branch block, LBBB). This results in contractile dyssynchrony (dyssynchronous heart failure, DHF), which further diminishes cardiac systolic function and energetic efficiency.

Cardiac Resynchronization Therapy

CRT is an established therapy for DHF patients. CRT typically employs bi-V pacing, with an endocardial right ventricular (RV) pacing lead and an epicardial LV pacing lead, to re-coordinate contraction (Bleeker et al., 2006a). CRT has been shown to acutely and chronically improve systolic function (Nelson et al., 2000) of the heart and to reverse the detrimental remodeling (Sutton et al., 2006) associated with heart failure. Clinical trials of CRT have consistently demonstrated improvement in heart failure symptoms, exercise tolerance, quality of life, and a reduction in recurrent hospitalizations (Auricchio et al., 2003).

Although CRT reduces morbidity and mortality (Cleland et al., 2005), approximately 30% of patients fail to respond to the therapy (Kass, 2005). This reflects the poor predictive capability of current approaches to identify potential responders to CRT. The QRS duration (QRS ≥150 ms), widely used in clinical trials as a basic component of the inclusion criteria for CRT, does not provide an indication of the degree of mechanical dyssynchrony (Fauchier et al., 2003). Indeed, patients with long QRS duration may not exhibit mechanical dyssynchrony and those with short QRS complexes may present with significant dyssynchrony in contraction (Auricchio et al., 1999; Fauchier et al., 2002; Pitzalis et al., 2002). Measurements of mechanical dyssynchrony by Doppler echocardiography (Bax et al., 2004; Yu et al., 2002) reveal only local dyssynchrony, while the complex deformations in DHF are global. In recent clinical trials, Doppler echocardiography was characterized by lack of repeatability and low predictive value (Beshai et al., 2007; Chung et al., 2008; Miyazaki et al.). The poor predictive capability of the above measures indicates an incomplete understanding of the relation between the electrical and mechanical events in DHF.

The presence of myocardial infarction (MI) is an additional reason for lack of response to CRT. Placement of a pacing electrode at or near the infarct scar may result in ineffective pacing and thus in failure of resynchronization. Since infarction modulates electromechanical interactions, it also alters the mechanism of CRT. Bleeker et al. (Bleeker et al., 2006b) documented that patients with transmural posterolateral scar have a much lower response rate to CRT than those without scar, 14% vs. 81%. Increased scar volume has been found to result in unfavorable response to CRT (Adelstein and Saba, 2007). Infarct location and scar transmurality are considered important (Choi et al., 2001; White et al., 2006) yet unknown factors that affect the relationship between electrical activation and contraction and contribute to diminished CRT efficacy.

Finally, the location of LV pacing has been shown to play an important role in CRT efficacy (Butter et al., 2000; Helm et al., 2007; St John Sutton et al., 2003). Currently, LV pacing lead is implanted in a tributary of the coronary sinus, as in epicardial bi-V pacing (Butter et al., 2001). However, for a small class of patients unsuitable for transvenous bi-V, a transseptal approach has been developed that allows endocardial bi-V pacing (Leclercq et al., 1999). Recent studies have brought to light the potential proarrhythmic effect of epicardial bi-V pacing (Fish et al., 2005), resulting from the reversal of the direction of electrical propagation in the LV. Furthermore, new findings indicate that endocardial bi-V pacing might be associated with improved resynchronization in canine models (Howard et al., 2011; van Deursen et al., 2009) and humans (Spragg et al., 2010). Thus determining the optimal location of LV pacing lead placement remains a problem.

Multi-scale computational modeling of electromechanics in the normal and failing heart is provided to address these problems according to some embodiments of the current invention. Recent advancements in cardiac computational modeling, numerical algorithms and image processing techniques have enabled the development of detailed tomographically-reconstructed heart models that integrate functions from the molecular level to the electromechanical interactions in the intact organ. According to this embodiment of the current invention, we employ such models to provide approaches to optimizing CRT therapy. To achieve this goal, this embodiment focuses on exploiting knowledge regarding the electromechanical delay in the heart as well as myocardial efficiency.

Electromechanical Delay in the Heart and how it can be Used to Optimize CRT

Significance of Electromechanical Delay

The time period between the local electrical depolarization and the onset of local myofiber shortening (mechanical activation) in the intact ventricles can last as much as tens of milliseconds. This electromechanical delay (EMD) is a function of the myocyte's intrinsic latent period between membrane depolarization and myofilament activation in the excitation-contraction process (Cordeiro et al., 2004), but is also dependent on the local myofiber mechanical loading conditions in the intact heart. Acute CRT therapy affects only the component of EMD that is due to the loading conditions, but has no influence on the cell-intrinsic E-C coupling latency (Russell et al., 2011). Thus, by understanding EMD and its distribution that is due to the loading conditions, one could suggest potential avenues for CRT optimization. Alternatively, since most echocardiography-based dyssynchrony measurements are affected by the timing of myofiber shortening onset, ascertaining the mechanisms underlying the EMD distribution may improve or lead to the development of novel indices of electromechanical dyssynchrony to identify potential CRT responders.

Electromechanical Delay in the Normal Heart

The first computational study to assess the 3D distribution of EMD was by Usyk and McCulloch (Usyk and McCulloch, 2003). In this study, the authors employed an electromechanical model of the normal canine ventricles to determine the 3D EMD distribution during sinus rhythm and following LV pacing. With this early model, which in fact was the first whole-heart electromechanical model developed, the authors demonstrated that EMD may be both positive and negative, indicating that myofiber shortening may precede electrical activation in the whole heart. A more recent study by Gurev et al. (Gurev et al., 2010) have expounded on this work by providing thorough analysis of the 3D EMD distribution in the normal rabbit heart and its dependence on the loading conditions (i.e. on the electrical activation sequence). Simulations of electromechanical activity during sinus rhythm and LV epicardial pacing were conducted and compared to determine the effect of electrical activation pattern on the 3D distribution of EMD. The simulation results revealed that the 3D distribution of EMD was heterogeneous and depended on the electrical activation sequence. The distributions were markedly different for sinus rhythm and epicardial pacing. During sinus rhythm, the distribution was longer at the epicardium compared to the endocardium and longer at the base compared to the apex. Following epicardial pacing, the distribution was markedly different: the posterior wall exhibited longer EMD compared to the anterior wall. Mechanistic analysis of the electromechanical behavior revealed that the late-depolarized regions were characterized with significant myofiber pre-stretch caused by the contraction of the early-depolarized regions. This pre-stretch, in turn, delayed myofiber shortening onset, and resulted in longer EMD there.

Assessment of EMD in DHF

The pumping inefficiency of the DHF heart arises from deleterious remodeling of cardiac electromechanical properties, from the sub-cellular to the organ level, and is thus expected to change the 3D EMD distribution. Determining the 3D EMD distribution in the setting of DHF and exploiting the mechanistic insight into the relation between electrical activation and mechanical contraction could offer clues to improvement in CRT delivery. In this section, we present our new image-based electromechanical model of the failing canine ventricles, and employ it to determine how the 3D distribution of EMD is altered in the setting of DHF according to an embodiment of the current invention.

Conclusions Regarding CRT Examples

A comprehensive characterization of the spatiotemporal electromechanical interactions in the DHF heart, without and with MI, is fundamental to the effort towards improving CRT efficacy. This example demonstrates that a biophysically-based model of ventricular electromechanics that incorporates representations from the scale of the protein to the intact organ is a powerful methodology to provide insight into the electromechanical interactions in the heart. This example highlights how the basic science insight into the electromechanical activity of the DHF heart gained from computational modeling can be exploited to guide improvements in CRT delivery according to an embodiment of the current invention. The simulation results presented here indicate that optimal CRT strategy in the DHF heart can be achieved by pacing at the LV location characterized with longest EMD. The same approach can be used to determine whether CRT can be also optimized by targeting the region with the longest EMD in the infarcted heart. In addition, computational modeling could also aid in the identification of the LV pacing location that results in maximal myocardial efficiency and most beneficial regional energy consumption. With new advancements in computational modeling and increased ubiquity of computers in the clinic, it will not be long before electromechanical models of DHF patients' hearts that are enriched with patient-specific data will serve as a bedside tool for diagnosis and treatment planning.

REFERENCES

1. Adelstein, E. C. and Saba, S. (2007) Scar Burden by Myocardial Perfusion Imaging Predicts Echocardiographic Response to Cardiac Resynchronization Therapy in Ischemic Cardiomyopathy. *Am Heart J* 153, 105-12.

2. Akar, F. G., Nass, R. D., Hahn, S., Cingolani, E., Shah, M., Hesketh, G. G., DiSilvestre, D., Tunin, R. S., Kass, D. A. and Tomaselli, G. F. (2007) Dynamic Changes in Conduction Velocity and Gap Junction Properties During Development of Pacing-Induced Heart Failure. *Am J Physiol Heart Circ Physiol* 293, H1223-30.

3. Akar, F. G., Spragg, D. D., Tunin, R. S., Kass, D. A. and Tomaselli, G. F. (2004) Mechanisms Underlying Conduction Slowing and Arrhythmogenesis in Nonischemic Dilated Cardiomyopathy. *Circ Res* 95, 717-25.

4. Ansalone, G., Giannantoni, P., Ricci, R., Trambaiolo, P., Fedele, F. and Santini, M. (2002) Doppler myocardial imaging to evaluate the effectiveness of pacing sites in patients receiving biventricular pacing. *J Am Coll Cardiol* 39, 489-99.

5. Ashikaga, H., Mickelsen, S. R., Ennis, D. B., Rodriguez, I., Kellman, P., Wen, H. and McVeigh, E. R. (2005) Electromechanical analysis of infarct border zone in chronic myocardial infarction. *Am J Physiol Heart Circ Physiol* 289, H1099-105.

6. Auricchio, A., Stellbrink, C., Block, M., Sack, S., Vogt, J., Bakker, P., Klein, H., Kramer, A., Ding, J., Salo, R., Tockman, B., Pochet, T. and Spinelli, J. (1999) Effect of Pacing Chamber and Atrioventricular Delay on Acute Systolic Function of Paced Patients with Congestive Heart Failure. The Pacing Therapies for Congestive Heart Failure Study Group. The Guidant Congestive Heart Failure Research Group. *Circulation* 99, 2993-3001.

7. Auricchio, A., Stellbrink, C., Butter, C., Sack, S., Vogt, J., Misier, A. R., Bocker, D., Block, M., Kirkels, J. H., Kramer, A. and Huvelle, E. (2003) Clinical Efficacy of Cardiac Resynchronization Therapy Using Left Ventricular Pacing in Heart Failure Patients Stratified by Severity of Ventricular Conduction Delay. *J Am Coll Cardiol* 42, 2109-16.

8. Bax, J. J., Bleeker, G. B., Marwick, T. H., Molhoek, S. G., Boersma, E., Steendijk, P., van der Wall, E. E. and Schalij, M. J. (2004) Left Ventricular Dyssynchrony Predicts Response and Prognosis after Cardiac Resynchronization Therapy. *J Am Coll Cardiol* 44, 1834-40.

9. Becker, R. A., Scher, A. M. and Erickson, R. V. (1958) Ventricular excitation in experimental left bundle branch block. *Am Heart J* 55, 547-56.

10. Beshai, J. F., Grimm, R. A., Nagueh, S. F., Baker, J. H., Beau, S. L., Greenberg, S. M., Pires, L. A. and Tchou, P. J. (2007) Cardiac-resynchronization therapy in heart failure with narrow QRS complexes. *N Eng Med* 357, 2461-2471.

11. Bleeker, G. B., Bax, J. J., Steendijk, P., Schalij, M. J. and van der Wall, E. E. (2006a) Left Ventricular Dyssynchrony in Patients with Heart Failure: Pathophysiology, Diagnosis and Treatment. *Nat Clin Pract Cardiovasc Med* 3, 213-9.

12. Bleeker, G. B., Kaandorp, T. A., Lamb, H. J., Boersma, E., Steendijk, P., de Roos, A., van der Wall, E. E., Schalij, M. J. and Bax, J. J. (2006b) Effect of Posterolateral Scar Tissue on Clinical and Echocardiographic Improvement after Cardiac Resynchronization Therapy. *Circulation* 113, 969-76.

13. Butter, C., Auricchio, A., Stellbrink, C., Fleck, E., Ding, J., Yu, Y., Huvelle, E. and Spinelli, J. (2001) Effect of Resynchronization Therapy Stimulation Site on the Systolic Function of Heart Failure Patients. *Circulation* 104, 3026-9.

14. Butter, C., Auricchio, A., Stellbrink, C., Schlegl, M., Fleck, E., Horsch, W., Huvelle, E., Ding, J. and Kramer, A. (2000) Should Stimulation Site Be Tailored in the Individual Heart Failure Patient? *Am J Cardiol* 86, 144K-151K.

15. Cheng, A., Nguyen, T. C., Malinowski, M., Daughters, G. T., Miller, D. C. and Ingels, N. B. (2008) Heterogeneity of left ventricular wall thickening mechanisms. *Circulation* 118, 713-721.

16. Choi, K. M., Kim, R. J., Gubernikoff, G., Vargas, J. D., Parker, M. and Judd, R. M. (2001) Transmural Extent of Acute Myocardial Infarction Predicts Long-Term Improvement in Contractile Function. *Circulation* 104, 1101-7.

17. Chung, E. S., Leon, A. R., Tavazzi, L., Sun, J. P., Nihoyannopoulos, P., Merlino, J., Abraham, W. T., Ghio, S., Leclercq, C. and Bax, J. J. (2008) Results of the Predictors of Response to CRT (PROSPECT) trial. *Circulation* 117, 2608-2616.

18. Cleland, J. G., Daubert, J. C., Erdmann, E., Freemantle, N., Gras, D., Kappenberger, L. and Tavazzi, L. (2005) The Effect of Cardiac Resynchronization on Morbidity and Mortality in Heart Failure. *N Engl J Med* 352, 1539-49.

19. Constantino, J., Gurev, V. and Trayanova, N. (2010) Optimal cardiac resynchronization therapy is achieved by pacing from the LV region with the longest electromechanical delay. *Heart Rhythm* 7, S164-165.

20. Cordeiro, J. M., Greene, L., Heilmann, C., Antzelevitch, D. and Antzelevitch, C. (2004) Transmural heterogeneity of calcium activity and mechanical function in the canine left ventricle. *Am J Physiol Heart Circ Physiol* 286, H1471-9.

21. Derval, N., Steendijk, P., Gula, L. J., Deplagne, A., Laborderie, J., Sacher, F., Knecht, S., Wright, M., Nault, I., Ploux, S., Ritter, P., Bordachar, P., Lafitte, S., Reant, P., Klein, G. J., Narayan, S. M., Garrigue, S., Hocini, M., Haissaguerre, M., Clementy, J. and Jais, P. (2010) Optimizing hemodynamics in heart failure patients by systematic screening of left ventricular pacing sites: the lateral left ventricular wall and the coronary sinus are rarely the best sites. *J Am Coll Cardiol* 55, 566-75.

22. Fauchier, L., Marie, O., Casset-Senon, D., Babuty, D., Cosnay, P. and Fauchier, J. P. (2002) Interventricular and Intraventricular Dyssynchrony in Idiopathic Dilated Cardiomyopathy: A Prognostic Study with Fourier Phase Analysis of Radionuclide Angioscintigraphy. *J Am Coll Cardiol* 40, 2022-30.

23. Fauchier, L., Marie, O., Casset-Senon, D., Babuty, D., Cosnay, P. and Fauchier, J. P. (2003) Reliability of QRS Duration and Morphology on Surface Electrocardiogram to Identify Ventricular Dyssynchrony in Patients with Idiopathic Dilated Cardiomyopathy. *Am J Cardiol* 92, 341-4.

24. Fish, J. M., Brugada, J. and Antzelevitch, C. (2005) Potential Proarrhythmic Effects of Biventricular Pacing. *J Am Coll Cardiol* 46, 2340-7.

25. Fung, J. W., Lam, Y. Y., Zhang, Q., Yip, G. W., Chan, W. W., Chan, G. C., Chan, J. Y. and Yu, C. M. (2009) Effect of left ventricular lead concordance to the delayed contraction segment on echocardiographic and clinical outcomes after cardiac resynchronization therapy. *J Cardiovasc Electrophysiol* 20, 530-5.

26. Gurev, V., Constantino, J., Rice, J. J. and Trayanova, N. A. (2010) Distribution of electromechanical delay in the heart: insights from a three-dimensional electromechanical model. *Biophys J* 99, 745-54.

27. Gurev, V., Lee, T., Constantino, J., Arevalo, H. and Trayanova, N. A. (2011) Models of cardiac electromechanics based on individual hearts imaging data: image-based electromechanical models of the heart. *Biomech Model Mechanobiol* 10, 295-306.

28. Helm, P. A., Younes, L., Beg, M. F., Ennis, D. B., Leclercq, C., Faris, O. P., McVeigh, E., Kass, D., Miller, M. I. and Winslow, R. L. (2006) Evidence of Structural Remodeling in the Dyssynchronous Failing Heart. *Circ Res* 98, 125-32.

29. Helm, R. H., Byrne, M., Helm, P. A., Daya, S. K., Osman, N. F., Tunin, R., Halperin, H. R., Berger, R. D., Kass, D. A. and Lardo, A. C. (2007) Three-Dimensional Mapping of Optimal Left Ventricular Pacing Site for Cardiac Resynchronization. *Circulation* 115, 953-61.

30. Hooks, D. A., Trew, M. L., Caldwell, B. J., Sands, G. B., LeGrice, I. J. and Smaill, B. H. (2007) Laminar Arrangement of Ventricular Myocytes Influences Electrical Behavior of the Heart. *Circ Res* 101, e103-12.

31. Howard, E. J., Covell, J. W., Mulligan, L. J., McCulloch, A. D., Omens, J. H. and Kerckhoffs, R. C. (2011) Improvement in pump function with endocardial biventricular pacing increases with activation time at the left ventricular pacing site in failing canine hearts. *Am J Physiol Heart Circ Physiol* 301, H1447-55.

32. Kaab, S., Nuss, H. B., Chiamvimonvat, N., O'Rourke, B., Pak, P. H., Kass, D. A., Marban, E. and Tomaselli, G. F. (1996) Ionic Mechanism of Action Potential Prolongation in Ventricular Myocytes from Dogs with Pacing-Induced Heart Failure. *Circ Res* 78, 262-73.

33. Kass, D. A. (2005) Cardiac Resynchronization Therapy. *J Cardiovasc Electrophysiol* 16 Suppl 1, S35-41.

34. Leclercq, C., Faris, O., Tunin, R., Johnson, J., Kato, R., Evans, F., Spinelli, J., Halperin, H., McVeigh, E. and Kass, D. A. (2002) Systolic improvement and mechanical resynchronization does not require electrical synchrony in the dilated failing heart with left bundle-branch block. *Circulation* 106, 1760-3.

35. Leclercq, F., Hager, F. X., Macia, J. C., Mariottini, C. J., Pasquie, J. L. and Grolleau, R. (1999) Left Ventricular Lead Insertion Using a Modified Transseptal Catheterization Technique: A Totally Endocardial Approach for Permanent Biventricular Pacing in End-Stage Heart Failure. *Pacing Clin Electrophysiol* 22, 1570-5.

36. LeGrice, I. J., Takayama, Y. and Covell, J. W. (1995) Transverse Shear Along Myocardial Cleavage Planes Provides a Mechanism for Normal Systolic Wall Thickening. *Circ Res* 77, 182-93.

37. Lindner, O., Sorensen, J., Vogt, J., Fricke, E., Baller, D., Horstkotte, D. and Burchert, W. (2006) Cardiac efficiency and oxygen consumption measured with 11C-acetate PET after long-term cardiac resynchronization therapy. *J Nucl Med* 47, 378-83.

38. Lindner, O., Vogt, J., Kammeier, A., Wielepp, P., Holzinger, J., Baller, D., Lamp, B., Hansky, B., Korfer, R., Horstkotte, D. and Burchert, W. (2005) Effect of cardiac resynchronization therapy on global and regional oxygen consumption and myocardial blood flow in patients with non-ischaemic and ischaemic cardiomyopathy. *Eur Heart J* 26, 70-6.

39. Lloyd-Jones, D., Adams, R., Carnethon, M., De Simone, G., Ferguson, T. B., Flegal, K., Ford, E., Furie, K., Go, A., Greenlund, K., Haase, N., Hailpern, S., Ho, M., Howard, V., Kissela, B., Kittner, S., Lackland, D., Lisabeth, L., Marelli, A., McDermott, M., Meigs, J., Mozaffarian, D., 39. Nichol, G., O'Donnell, C., Roger, V., Rosamond, W., Sacco, R., Sorlie, P., Stafford, R., Steinberger, J., Thom, T., Wasserthiel-Smoller, S., Wong, N., Wylie-Rosett, J. and Hong, Y. (2009) Heart Disease and Stroke Statistics-2009 Update: A Report from the American Heart Association Statistics Committee and Stroke Statistics Subcommittee. *Circulation* 119, 480-6.

40. Marijianowski, M. M., Teeling, P., Mann, J. and Becker, A. E. (1995) Dilated Cardiomyopathy Is Associated with an Increase in the Type I/Type III Collagen Ratio: A Quantitative Assessment. *J Am Coll Cardiol* 25, 1263-72.

41. Miyazaki, C., Redfield, M. M., Powell, B. D., Lin, G. M., Herges, R. M., Hodge, D. O., Olson, L. J., Hayes, D. L., Espinosa, R. E., Rea, R. F., Bruce, C. J., Nelson, S. M., Miller, F. A. and Oh, J. K. (2010) Dyssynchrony indices to predict response to cardiac resynchronization therapy: a comprehensive prospective single-center study. *Circ Heart Fail* 3, 565-73.

42. Nelson, G. S., Berger, R. D., Fetics, B. J., Talbot, M., Spinelli, J. C., Hare, J. M. and Kass, D. A. (2000) Left Ventricular or Biventricular Pacing Improves Cardiac Function at Diminished Energy Cost in Patients with Dilated Cardiomyopathy and Left Bundle-Branch Block. *Circulation* 102, 3053-9.

43. O'Rourke, B., Kass, D. A., Tomaselli, G. F., Kaab, S., Tunin, R. and Marban, E. (1999) Mechanisms of Altered Excitation-Contraction Coupling in Canine Tachycardia-Induced Heart Failure, I: Experimental Studies. *Circ Res* 84, 562-70.

44. Pitzalis, M. V., Iacoviello, M., Romito, R., Massari, F., Rizzon, B., Luzzi, G., Guida, P., Andriani, A., Mastropasqua, F. and Rizzon, P. (2002) Cardiac Resynchronization Therapy Tailored by Echocardiographic Evaluation of Ventricular Asynchrony. *J Am Coll Cardiol* 40, 1615-22.

45. Rice, J. J., Wang, F., Bers, D. M. and de Tombe, P. P. (2008) Approximate model of cooperative activation and crossbridge cycling in cardiac muscle using ordinary differential equations. *Biophys J* 95, 2368-90.

46. Russell, K., Smiseth, O. A., Gjesdal, O., Qvigstad, E., Norseng, P. A., Sjaastad, I., Opdahl, A., Skulstad, H., Edvardsen, T. and Remme, E. W. (2011) Mechanism of prolonged electromechanical delay in late activated myocardium during left bundle branch block. *Am J Physiol Heart Circ Physiol* 301, H2334-43.

47. Spragg, D. D., Dong, J., Fetics, B. J., Helm, R., Marine, J. E., Cheng, A., Henrikson, C. A., Kass, D. A. and Berger, R. D. (2010) Optimal left ventricular endocardial pacing sites for cardiac resynchronization therapy in patients with ischemic cardiomyopathy. *J Am Coll Cardiol* 56, 774-81.

48. St John Sutton, M. G., Plappert, T., Abraham, W. T., Smith, A. L., DeLurgio, D. B., Leon, A. R., Loh, E., Kocovic, D. Z., Fisher, W. G., Ellestad, M., Messenger, J., Kruger, K., Hilpisch, K. E. and Hill, M. R. (2003) Effect of Cardiac Resynchronization Therapy on Left Ventricular Size and Function in Chronic Heart Failure. *Circulation* 107, 1985-90.

49. Suffoletto, M. S., Dohi, K., Cannesson, M., Saba, S. and Gorcsan, J., 3rd. (2006) Novel speckle-tracking radial strain from routine black-and-white echocardiographic images to quantify dyssynchrony and predict response to cardiac resynchronization therapy. *Circulation* 113, 960-8.

50. Suga, H. (1990) Ventricular energetics. *Physiol Rev* 70, 247-77.

51. Sutton, M. G., Plappert, T., Hilpisch, K. E., Abraham, W. T., Hayes, D. L. and Chinchoy, E. (2006) Sustained Reverse Left Ventricular Structural Remodeling with Cardiac Resynchronization at One Year Is a Function of Etiology: Quantitative Doppler Echocardiographic Evidence from the Multicenter Insync Randomized Clinical Evaluation (MIRACLE). *Circulation* 113, 266-72.

52. Tyberg, J. V., Yeatman, L. A., Parmley, W. W., Urschel, C. W. and Sonnenblick, E. H. (1970) Effects of hypoxia on mechanics of cardiac contraction. *Am J Physiol* 218, 1780-8.

53. Ukkonen, H., Beanlands, R. S., Burwash, I. G., de Kemp, R. A., Nahmias, C., Fallen, E., Hill, M. R. and Tang, A. S. (2003) Effect of cardiac resynchronization on myocardial efficiency and regional oxidative metabolism. *Circulation* 107, 28-31.

54. Usyk, T. P. and McCulloch, A. D. (2003) Relationship between Regional Shortening and Asynchronous Electrical Activation in a Three-Dimensional Model of Ventricular Electromechanics. *J Cardiovasc Electrophysiol* 14, S196-202.

55. Vadakkumpadan, F., Arevalo, H., Prassl, A. J., Chen, J., Kickinger, F., Kohl, P., Plank, G. and Trayanova, N. (2010) Image-based models of cardiac structure in health and disease. *Wiley Interdiscip Rev Syst Biol Med* 2, 489-506.

56. van Deursen, C., van Geldorp, I. E., Rademakers, L. M., van Hunnik, A., Kuiper, M., Klersy, C., Auricchio, A. and Prinzen, F. W. (2009) Left ventricular endocardial pacing improves resynchronization therapy in canine left bundle-branch hearts. *Circ Arrhythm Electrophysiol* 2, 580-7.

57. Walker, J. C., Ratcliffe, M. B., Zhang, P., Wallace, A. W., Fata, B., Hsu, E. W., Saloner, D. and Guccione, J. M. (2005) MRI-based finite-element analysis of left ventricular aneurysm. *Am J Physiol Heart Circ Physiol* 289, H692-700.

58. White, J. A., Yee, R., Yuan, X., Krahn, A., Skanes, A., Parker, M., Klein, G. and Drangova, M. (2006) Delayed Enhancement Magnetic Resonance Imaging Predicts Response to Cardiac Resynchronization Therapy in Patients with Intraventricular Dyssynchrony. *J Am Coll Cardiol* 48, 1953-60.

59. Wu, Y., Bell, S. P., Trombitas, K., Witt, C. C., Labeit, S., LeWinter, M. M. and Granzier, H. (2002) Changes in Titin Isoform Expression in Pacing-Induced Cardiac Failure Give Rise to Increased Passive Muscle Stiffness. *Circulation* 106, 1384-9.

60. Yu, C. M., Chau, E., Sanderson, J. E., Fan, K., Tang, M. O., Fung, W. H., Lin, H., Kong, S. L., Lam, Y. M., Hill, M. R. and Lau, C. P. (2002) Tissue Doppler Echocardiographic Evidence of Reverse Remodeling and Improved Synchronicity by Simultaneously Delaying Regional Contraction after Biventricular Pacing Therapy in Heart Failure. *Circulation* 105, 438-45.

61. H. Ashikaga, H. Arevalo, F. Vadakkumpadan, R. C. B. III, J. D. Bayer, S. Nazarian, M. M. Zviman, H. Tandri, R. D. Berger, H. Calkins, D. A. Herzka, N. A. Trayanova, H. R. Halperin, Feasibility of image-based simulation to estimate ablation target in human ventricular arrhythmia, Heart Rhythm, 10 (2013), pp. 1109-1116

62. O. Mesubi, G. Ahmad, J. Jeudy, A. Jimenez, R. Kuk, A. Saliaris, V. See, S. Shorofsky, T. Dickfield, Impact of ICD Artifact Burden on Late Gadolinium Enhancement Cardiac MR Imaging in Patients Undergoing Ventricular Tachycardia Ablation. Pacing and Clinical Electrophysiology, 37 (2014), pp. 1274-1283

63. Tusscher et al., AJP—HeartCirc. Phys., 286:1673-1698, 2004

64. Pu et al, CircRes, 81:110-119, 1997

65. Dun et al., AJP—HeartCirc. Phys., 287:1046-1064, 2004

66. Jiang et al., Cardiovasc. Res., 48:34-43, 2000.

67. Yao et al, Circ. Res., 92:437-443, 2003.

68. Vivek Y. Reddy, Matthew R. Reynolds, Petr Neuzil, Allison W. Richardson, Milos Taborsky, Krit Jongnarangsin, Stepan Kralovec, Lucie Sediva, Jeremy N. Ruskin, Mark E. Josephson, Prophylactic Catheter Ablation for the Prevention of Defibrillator Therapy, N Engl J Med, 357 (2007), pp. 2657-2665

69. Saman Nazarian, CMR for Mapping the Missing Dimension in Ventricular Tachycardia Ablation☐, JACC: Cardiovascular Imaging 3 (3) (2010), pp. 286-288.

70. Wellens H J. Catheter ablation of cardiac arrhythmias: usually cure, but complications may occur. Circulation. 99 (1999), pp 195-197

71. H. Arevalo, G. Plank, P. Helm, H. Halperin, N. Trayanova, Tachycardia in post-infarction hearts: insights from 3d image-based ventricular models, PLoS ONE, 8 (2013), p. e68872.

72. T. Sasaki, R. Hansford, M. M. Zviman, A. Kolandaivelu, D. A. Bluemke, R. D. Berger, H. Calkins, H. R. Halperin, S. Nazarian, Quantitative Assessment of Artifacts on Cardiac Magnetic Resonance Imaging of Patients With Pacemakers and Implantable Cardioverter-Defibrillators, Circulation: Cardiovascular Imaging, 4 (2011), pp. 662-670

The above provides some examples according to particular embodiments of the current invention. The broad concepts of the current invention are not limited to only these particular examples. More generally, a method of planning a patient-specific cardiac procedure according to an embodiment of the current invention includes receiving three-dimensional imaging data of a patient's heart, simulating at least one of electrophysiological or electromechanical activity of at least a portion of the patient's heart using the three-dimensional imaging data, and planning the patient-specific cardiac procedure based on the simulating. The cardiac procedure is for providing a preselected alteration of at least one of electrophysiological or electromechanical behavior of the patient's heart.

The three-dimensional imaging data can be MRI data as described in the examples above. However, the broad concepts of the current invention are not limited to that particular example. The three-dimensional imaging data can be can be at least one of magnetic resonance imaging (MRI), computed tomography (CT), positron emission tomography (PET), ultrasound, or nuclear tracer three-dimensional imaging data, for example. The method of planning a patient-specific cardiac procedure can further include receiving additional patient-specific data in addition to the three-dimensional imaging data. For example, some embodiments can include receiving at least one of biopsy data, electrocardiogram data, recorded data from an implantable device (pace maker, defibrillator, etc.), or invasive electrical mapping data (e.g., endoscopic). The simulating can then use the additional patient-specific data for the simulation.

The simulating at least one of electrophysiological or electromechanical activity of at least the portion of the patient's heart can include constructing a geometric model of the portion of the patient's heart. The geometric model can include normal tissue regions and remodeled tissue regions that are determined for the patient using the three-dimensional imaging data. The term "remodeled tissue" can include infarct scar, infarct border (gray) zone, fibrosis, or other disease-related structural, electrophysiological or contractile changes in the heart. The simulating can further include estimating tissue fiber orientations in the geometric model of the portion of the patient's heart. The estimation of fiber orientations can be done in a variety of ways. For example, the fiber orientations can be calculated using a Laplace-Dirichlet method to define the local transmural and apicobasal axes at each spatial location in the ventricles, (J. D. Bayer, R. Blake, G. Plank, Trayanova N, Novel rule based algorithm for assigning myocardial fiber orientation to computation heart models. *Ann Biomed Eng.*, (in review) (2012), the entire contents of which are incorporated herein by reference). Another approach could utilize pre-compiled data (i.e., atlas data), which can be mapped into the specific size and shape of the patient's heart (Image-Based Estimation of Ventricular Fiber Orientations for Personalized Modeling of Cardiac Electrophysiology, Vadakkumpadan F, Arevalo H, Ceritoglu C, Miller M, Trayanova N., IEEE Trans Med Imaging. 2012 Jan. 18. [Epub ahead of print], the entire contents of which are incorporated herein by reference).

A method of planning a patient-specific cardiac procedure according to an embodiment of the current invention can be directed to planning an ablation procedure to alleviate a ventricular arrhythmia. In this embodiment, the geometric model of the at least said portion of the patient's heart includes at least a geometric model of right and left ventricles of the patient's heart. The remodeled tissue regions in this case can be segmented into a plurality of different regions based on the three-dimensional imaging data. The plurality of different regions can include scar tissue regions, normal tissues regions, and transition zones, for example, between normal and scar tissue regions. The transition zones include infarct border zone tissue regions (we also refer to these zones as GZ, gray zones). The simulating in this case can be simulating electrophysiological activity of at least the right and left ventricles of the patient's heart. The ventricular arrhythmia can be ventricular tachycardia or ventricular fibrillation, for example. In an embodiment of the current invention, the planning of the patient-specific cardiac procedure includes identifying organizing centers of ventricular tachycardia from the simulation of electrophysiological activity. In some embodiments, the planning the patient-specific cardiac procedure can include identifying a critical pathway for ventricular tachycardia or three-dimensional scroll-wave filaments corresponding to the organizing centers as well as other slow conducting pathways through and around areas of scar tissue that are a part of a ventricular tachycardia circuit and further planning ablation to coincide with at least a portion of the three-dimensional scroll-wave filaments or other critical pathways for the ventricular tachycardia. (See above for some specific examples.)

In a method of planning a patient-specific cardiac procedure according to other embodiments of the current invention, the geometric model of the portion of the patient's heart includes a geometric model of at least right and left atria of the patient's heart. In this embodiment, the remodeled tissue regions are fibrotic tissue regions. The simulating at least one of electrophysiological or electromechanical activity is simulating electrophysiological activity of at least the right and left atria of the patient's heart. This embodiment is for planning an ablation procedure to alleviate atrial fibrillation. In another embodiment, the simulating at least one of electrophysiological or electromechanical activity is simulating electromechanical activity of at least a portion of the patient's heart. The planning can include determining whether the patient is a suitable candidate for cardiac resynchronization therapy. If the patient is a suitable candidate for cardiac resynchronization therapy, further embodiments can include planning a location in which to attach at least one pacing lead for cardiac resynchronization therapy. Further embodiments can include, planning the location in which to attach at least one pacing lead for cardiac resynchronization therapy based on regions of longest electromechanical delay or regions of latest electrical or mechanical activation as determined from the simulation. Further embodiments can include, planning the location in which to attach at least one pacing lead for cardiac resynchronization therapy based on local or global energy consumption or myocardial efficiency, as determined from the simulation. Myocardial efficiency is the ratio of mechanical work performed by the ventricles to myocardial energy consumption.

We claim:

1. A computer implemented method of non-invasively simulating a subject-specific cardiac procedure, comprising:
receiving three-dimensional imaging data of a subject's heart, the subject having an ICD, wherein said ICD causes an imaging artifact in said three-dimensional imaging data of said subject's heart, said three-dimensional imaging data including regions that are free of said artifact and regions that are affected by said artifact;
segmenting said regions of said three-dimensional imaging data that are free of said artifact into a plurality of normal tissue regions and remodeled tissue regions for said subject;
extrapolating from said regions of said three-dimensional imaging data that are free of said artifact to provide extrapolated three-dimensional imaging data corresponding to said regions that are affected by said artifact; and
simulating at least one of electrophysiological or electromechanical activity of at least a portion of said subject's heart using said segmented and extrapolated three-dimensional imaging data, said simulating including providing a preselected alteration of at least one of electrophysiological or electromechanical behavior of said subject's heart for a target of said subject-specific cardiac ablation procedure.

2. A computer implemented method of non-invasively simulating a subject-specific cardiac procedure according to claim 1, wherein said simulating at least one of electrophysiological or electromechanical activity of at least said portion of said subject's heart comprises constructing a geometric model of said at least said portion of said subject's heart, said geometric model including normal tissue regions and remodeled tissue regions determined for said subject using said three-dimensional imaging data.

3. A computer implemented method of non-invasively simulating a subject-specific cardiac procedure according to claim 2, wherein said simulating at least one of electrophysiological or electromechanical activity of at least said portion of said subject's heart further comprises estimating tissue fiber orientations in said geometric model of said at least said portion of said subject's heart.

4. A computer implemented method of non-invasively simulating a subject-specific cardiac procedure according to claim 3, wherein said geometric model of said at least said portion of said subject's heart includes at least a geometric model of right and left ventricles of said subject's heart,
wherein said remodeled tissue regions are segmented into a plurality of different regions based on said three-dimensional imaging data, said plurality of different regions including imaging data consistent with scar tissue regions, normal tissues regions, and transition zones between normal and scar tissue regions, the transition zones including infarct border zone tissue regions,
wherein said simulating at least one of electrophysiological or electromechanical activity is simulating electrophysiological activity of at least said right and left ventricles of said subject's heart, and
wherein said simulating said subject-specific cardiac procedure includes planning an ablation procedure to alleviate a ventricular arrhythmia.

5. A computer implemented method of non-invasively simulating a subject-specific cardiac procedure according to claim 4, wherein said planning said subject-specific cardiac procedure comprises identifying organizing centers of ventricular tachycardia or areas of conduction block or slow conduction from said simulating electrophysiological activity of at least said right and left ventricles of said subject's heart.

6. A computer implemented method of non-invasively simulating a subject-specific cardiac procedure according to claim 5, wherein said planning said subject-specific cardiac procedure comprises identifying a critical pathway for ventricular tachycardia or three-dimensional scroll-wave filaments corresponding to said organizing centers as well as other slow conducting pathways or areas of conduction block through and around areas of scar tissue that are a part of a ventricular tachycardia circuit, and wherein said planning said subject-specific cardiac procedure further comprises planning ablation to coincide with at least a portion of said three-dimensional scroll-wave filaments or other critical pathways for said ventricular tachycardia.

7. A computer implemented method of non-invasively simulating a subject-specific cardiac procedure according to claim 1, wherein said extrapolating includes interpolating from contours of said imaging artifact.

8. A computer implemented method of non-invasively simulating a subject-specific cardiac procedure according to claim 7, wherein said extrapolating includes assigning normal tissue to said regions that are affected by said artifact.

9. A non-transient computer-readable medium comprising computer-executable code that, when executed by a computer, causes the computer to perform:
receiving three-dimensional imaging data of a subject's heart, the subject having an ICD, wherein said ICD causes an imaging artifact in said three-dimensional imaging data of said subject's heart, said three-dimensional imaging data including regions that are free of said artifact and regions that are affected by said artifact;
segmenting said regions of said three-dimensional imaging data that are free of said artifact into a plurality of normal tissue regions and remodeled tissue regions for said subject;
extrapolating from said regions of said three-dimensional imaging data that are free of said artifact to provide extrapolated three-dimensional imaging data corresponding to said regions that are affected by said artifact; and
non-invasively simulating at least one of electrophysiological or electromechanical activity of at least a portion of said subject's heart using said segmented and extrapolated three-dimensional imaging data, said simulating including providing a preselected alteration of at least one of electrophysiological or electromechanical behavior of said subject's heart for a target of said subject-specific cardiac ablation procedure.

10. The non-transient computer-readable medium of claim 9, wherein said simulating at least one of electrophysiological or electromechanical activity of at least said portion of said subject's heart comprises constructing a geometric model of said at least said portion of said subject's heart, said geometric model including normal tissue regions and remodeled tissue regions determined for said subject using said three-dimensional imaging data.

11. The non-transient computer-readable medium of claim 10, wherein said simulating at least one of electrophysiological or electromechanical activity of at least said portion of said subject's heart further comprises estimating tissue fiber orientations in said geometric model of said at least said portion of said subject's heart.

12. The non-transient computer-readable medium of claim 11, wherein said geometric model of said at least said portion of said subject's heart includes at least a geometric model of right and left ventricles of said subject's heart,
wherein said remodeled tissue regions are segmented into a plurality of different regions based on said three-dimensional imaging data, said plurality of different regions including imaging data consistent with scar tissue regions, normal tissues regions, and transition zones between normal and scar tissue regions, the transition zones including infarct border zone tissue regions,
wherein said simulating at least one of electrophysiological or electromechanical activity is simulating electrophysiological activity of at least said right and left ventricles of said subject's heart, and
wherein said simulating said subject-specific cardiac procedure includes planning an ablation procedure to alleviate a ventricular arrhythmia.

13. The non-transient computer-readable medium of claim 12, wherein said planning said subject-specific cardiac procedure comprises identifying organizing centers of ventricular tachycardia or areas of conduction block or slow conduction from said simulating electrophysiological activity of at least said right and left ventricles of said subject's heart.

14. The non-transient computer-readable medium of claim 13, wherein said planning said subject-specific cardiac procedure comprises identifying a critical pathway for ventricular tachycardia or three-dimensional-scroll-wave filaments corresponding to said organizing centers as well as other slow conducting pathways or areas of conduction block through and around areas of scar tissue that are a part of a ventricular tachycardia circuit, and wherein said planning said subject-specific cardiac procedure further comprises planning ablation to coincide with at least a portion of said three-dimensional scroll-wave filaments or other critical pathways for said ventricular tachycardia.

15. The non-transient computer-readable medium of claim 9, wherein said extrapolating includes interpolating from contours of said imaging artifact.

16. The non-transient computer-readable medium of claim 15, wherein said extrapolating includes assigning normal tissue to said regions that are affected by said imaging artifact.

17. A system comprising a computer, said computer comprising a non-transient computer-readable medium comprising computer-executable code that, when executed by the computer, causes the computer to perform:
receiving three-dimensional imaging data of a subject's heart, the subject having an ICD, wherein said ICD causes an imaging artifact in said three-dimensional imaging data of said subject's heart, said three-dimensional imaging data including regions that are free of said artifact and regions that are affected by said artifact;
segmenting said regions of said three-dimensional imaging data that are free of said artifact into a plurality of normal tissue regions and remodeled tissue regions for said subject;
extrapolating from said regions of said three-dimensional imaging data that are free of said artifact to provide extrapolated three-dimensional imaging data corresponding to said regions that are affected by said artifact; and
non-invasively simulating at least one of electrophysiological or electromechanical activity of at least a portion of said subject's heart using said segmented and extrapolated three-dimensional imaging data, said simulating including providing a preselected alteration of at least one of electrophysiological or electromechanical behavior of said subject's heart for a target of said subject-specific cardiac ablation procedure.

18. The system of claim 17, wherein said simulating at least one of electrophysiological or electromechanical activity of at least said portion of said subject's heart comprises constructing a geometric model of said at least said portion of said subject's heart, said geometric model including normal tissue regions and remodeled tissue regions determined for said subject using said three-dimensional imaging data.

19. The system of claim 18, wherein said simulating at least one of electrophysiological or electromechanical activity of at least said portion of said subject's heart further comprises estimating tissue fiber orientations in said geometric model of said at least said portion of said subject's heart.

20. The system of claim 19, wherein said geometric model of said at least said portion of said subject's heart includes at least a geometric model of right and left ventricles of said subject's heart,
wherein said remodeled tissue regions are segmented into a plurality of different regions based on said three-dimensional imaging data, said plurality of different regions including imaging data consistent with scar tissue regions, normal tissues regions, and transition zones between normal and scar tissue regions, the transition zones including infarct border zone tissue regions,
wherein said simulating at least one of electrophysiological or electromechanical activity is simulating electrophysiological activity of at least said right and left ventricles of said subject's heart, and
wherein said simulating said subject-specific cardiac procedure includes planning an ablation procedure to alleviate a ventricular arrhythmia.

21. The system of claim 20, wherein said planning said subject-specific cardiac procedure comprises identifying organizing centers of ventricular tachycardia or areas of conduction block or slow conduction from said simulating electrophysiological activity of at least said right and left ventricles of said subject's heart.

22. The system of claim 21, wherein said planning said subject-specific cardiac procedure comprises identifying a critical pathway for ventricular tachycardia or three-dimensional scroll-wave filaments corresponding to said organizing centers as well as other slow conducting pathways or areas of conduction block through and around areas of scar tissue that are a part of a ventricular tachycardia circuit, and wherein said planning said subject-specific cardiac procedure further comprises planning ablation to coincide with at least a portion of said three-dimensional scroll-wave filaments or other critical pathways for said ventricular tachycardia.

23. The system of claim 17, wherein said extrapolating includes interpolating from contours of said imaging artifact.

24. The system of claim 23, wherein said extrapolating includes assigning normal tissue to said regions that are affected by said imaging artifact.

* * * * *